US007113819B2

(12) United States Patent  
Hamilton et al.

(10) Patent No.: US 7,113,819 B2
(45) Date of Patent: Sep. 26, 2006

(54) METHOD AND APPARATUS FOR MONITORING THE CONDITION OF A FETUS

(75) Inventors: Emily F. Hamilton, Nun's Island (CA); Michael C. Glaude, Anjou (CA); Maciej Macieszczak, Kanata (CA); Philip A. Warrick, Montreal (CA)

(73) Assignee: LMS Medical Systems Ltd., Montreal (CA)

( * ) Notice: Subject to any disclaimer, the term of this patent is extended or adjusted under 35 U.S.C. 154(b) by 476 days.

(21) Appl. No.: 10/113,788

(22) Filed: Apr. 1, 2002

(65) Prior Publication Data

US 2003/0187364 A1  Oct. 2, 2003

(51) Int. Cl.
 *A61B 5/04* (2006.01)
(52) U.S. Cl. .................................... 600/511
(58) Field of Classification Search ............... 600/376, 600/511, 378, 453; 128/898
 See application file for complete search history.

(56) References Cited

U.S. PATENT DOCUMENTS

| | | | |
|---|---|---|---|
| 3,703,168 A | 11/1972 | Frink | |
| 3,989,034 A | 11/1976 | Hojaiban | |
| 4,510,944 A | 4/1985 | Porges | |
| 4,964,410 A * | 10/1990 | Leahey et al. | 600/509 |
| 5,442,940 A | 8/1995 | Secker et al. | |
| 5,494,032 A | 2/1996 | Robinson et al. | |
| 5,596,993 A | 1/1997 | Oriol et al. | |
| 5,609,156 A * | 3/1997 | Keith et al. | 600/483 |
| 5,666,959 A | 9/1997 | Deans et al. | |
| 5,724,032 A | 3/1998 | Klein et al. | |
| 5,749,831 A | 5/1998 | Baker | |
| 5,817,035 A * | 10/1998 | Sullivan | 600/588 |
| 5,846,189 A | 12/1998 | Pincus | |
| 5,954,663 A | 9/1999 | Gat | |
| 5,957,855 A | 9/1999 | Oriol et al. | |
| 6,254,537 B1 | 7/2001 | Nguyen | |
| 6,585,645 B1 * | 7/2003 | Hutchinson | 600/300 |
| 2001/0014776 A1 | 8/2001 | Oriol et al. | |
| 2002/0193670 A1 * | 12/2002 | Garfield et al. | 600/304 |

FOREIGN PATENT DOCUMENTS

EP          0522674          1/1993

(Continued)

OTHER PUBLICATIONS

Emily Hamilton et al. ; "Intrapartum Prediction of Fetal Status and Assessment of Labour Progress; Bailliere's Clinical Obstetrics and Gynecology"; vol. 8, No. 3, Sep. 1994; pp. 567-581.

(Continued)

*Primary Examiner*—George Manuel
*Assistant Examiner*—Lenwood Faulcon
(74) *Attorney, Agent, or Firm*—Ladas & Parry LLP

(57) ABSTRACT

A method and apparatus for monitoring the condition of a fetus to assess a degree of risk of developing a permanent neurological condition is provided. A signal indicative of a fetal heart is processed to derive a degree of risk of developing a permanent neurological condition. The data indicative of the degree of risk of developing a permanent neurological condition indicates a likelihood that the condition of the fetus belongs to a class in a group of classes, where each class in the group of classes is associated with a pre-defined fetal condition. Data indicative of the degree of risk of developing a permanent neurological condition is then released. In one example, a neural network is used to obtain data indicating the likelihood that the condition of the fetus belongs to a class in the group of classes.

75 Claims, 10 Drawing Sheets

FOREIGN PATENT DOCUMENTS

| | | |
|---|---|---|
| EP | 0 310 349 | 4/1994 |
| EP | 0 564 459 | 5/1996 |

OTHER PUBLICATIONS

Emily Hamilton et al.; "Dystocia Among Women with Symptomatic Uterine Rupture"; Dept. of Obstetrics and Gynecology; Mar. 2001; vol. 184, No. 4;; pp. 620-624;l.

Emily Hamilton et al.; "An application of Real Time Decision Support in Obstetrics"; Department of Obstetrics and Gynecology; Aug. 23, 1994; pp. 446-455.

E. Hamilton et al.; "A Comprehensive Labor Surveillance System"; Jewish General Hospital; 1987.

"Summary of Safety and Effectiveness"; Series 50 OB TraceVue; Oct. 3, 1997.

Oxford Instruments Medical Ltd.; Apr. 27, 2001; 510(k) Summary. Collection of abstracts obtained in search on Feb. 4, 2002.

Lawrence Devoe et al.; "A Comparison of Visual Analyses of Intrapartum Fetal Heart Rate Tracings According to the New National Institute of Child Health and Human Development guidelines with Computer Analyses by an Automated Fetal Heart Rate Monitoring System"; Jan. 22-25, 2000; pp. 361-366.

Low, James A. et al., *Motor and cognitive deficits after intrapartum asphyxia in the mature fetus, Am J Obstet Gynecol*, vol. 158, No. 2 (Feb. 1988), pp. 356-361.

Badawi, Nadia et al., *Antepartum risk factors for newborn encephalopathy: the Western Australian case-control study, BMJ*, vol. 317 (Dec. 5, 1998), pp. 1549-1558.

Low, James A., *The role of blood gas and acid-base assessment in the diagnosis of intrapartum fetal asphyxia, Am J Obstet Gynecol*, vol. 159, No. 5 (Nov. 1988), pp. 1235-1240.

Sarnat, Harvey B. et al., *Neonatal Encephalopathy Following Fetal Distress, Arch Neurol*, vol. 33 (Oct. 1976), pp. 696-705.

Mantel, R. et al., *Computer analysis of antepartum fetal heart rate: 1. Baseline determination, Int J Biomed Comput*, Elsevier Scientific Publishers Ireland Ltd., vol. 25 (1990), pp. 261-286.

Sloan, Frank A., *The influence of obstetric no-fault compensation on obstetricians' practice patterns, American Journal of Obstetrics and Gynecology*, Sep. 1998—Part I, vol. 179, No. 3, pp. 671-676.

"Neonatal encephalopathies, time to reconsider the cause of neonatal encephalopathies", BMJ, vol. 317 (Dec. 5, 1998), pp. 1537-1538.

\* cited by examiner

CLASS A:  75%
CLASS B:  20%
CLASS C:  3%
CLASS D:  2%

FIG. 2A

CLASS A:  75%

FIG. 2B

→ THE FETUS SHOWS A HIGH LIKELIHOOD OF EXHIBITORY NEW-BORN ENCEPHELOPETHY BUT THE BASE DEFICIT IS ABOVE THE CRITICAL LEVEL.

FIG. 2C

METHOD AND APPARATUS FOR MONITORING THE CONDITION OF A FETUS

FIELD OF THE INVENTION

The present invention relates generally to electronic fetal monitoring and, more particularly, to a method and apparatus for classifying a fetal heart rate signal to assess a degree of risk for permanent neurological damage associated to the fetus.

BACKGROUND OF THE INVENTION

During labour, a fetus may experience oxygen deprivation that can produce permanent neurological damage. Cerebral palsy (CP) is a permanent neurological condition characterised by neuromotor spasticity and often associated with seizures and or mental retardation. In severe forms the child may be unable to crawl, have frequent seizures and severe mental handicap. Brain injury from insufficient oxygenation of the baby during labor leading to cerebral palsy is a condition obstetricians wish to avoid. Typically, since the fetus is not easily accessible and therefore evaluation is based on indirect observations, the medical team evaluates indirect signs of insufficient oxygenation of the baby during labour and may intervene with various diagnostic or therapeutic options to avoid serious fetal compromise.

One of the most commonly used methods to evaluate fetal tolerance to labour is analysis of the fetal heart rate by using electronic fetal monitors. These monitors measure both the fetal heart rate and the mother's uterine contraction pattern. They produce a paper print out of the tracing over time. Historically, the clinical staff used visual methods to study the tracings and from this deduce the degree of fetal well being in regards to tolerance to labour or pre-labour conditions. Abnormal patterns can lead to interventions such as more diagnostic tests, induced delivery of the baby or delivery by cesarean section. The features of the fetal heart rate that are used by clinicians include baseline, accelerations, deceleration and variability of the fetal heart rate.

A deficiency with the above described method is that it does not allow to objectively quantify multiple features of tracings over time since the analysis of the strip by the doctor or nurse is visual and therefore subject to imprecision and normal human biases. Physicians show great variation in how they measure, label and interpret fetal heart rate patterns, particularly when the patterns are measured only by visual inspection of the paper recording. While doctors and nurses are trained and presumably competent in their ability to assess the strip, there can be differences of opinion that may result in different interventions being done to the patient. There is often no suitable confirmation of the preoperative diagnosis that can be used to objectively validate the doctor's decision.

The issue of whether severe neurological damage could have been prevented with a suitable diagnosis is the issue of several lawsuits in the United Kingdom and in the United States. Due to the lack of objective and reliable data, the actions of the health care team are frequently considered not defensible and several cases are settled out of court. Irrespective of the exact proportions of preventable cases, the total malpractice cost born by obstetricians is staggering. Total annual estimated cost by the Florida Neurologic compensation Board for the labor & delivery related injuries or death was (no fault cost 27.5$ million per year). Births in Florida represent 4% of the total US births. Extrapolating these rates to the entire United States, the cost of birth related brain injury is approximately 650 million USD annually without accounting for the human cost. For additional information pertaining to the above, the reader is invited to refer to Frank A. Sloan, PhD[a], Kathryn Whetten-Goldstein, PhD[b], Gerald B. Hickson, MD[c], *The influence of obstetric no-fault compensation on obstetricians' practice patterns*, American Journal of Obstetrics and Gynecology September 1998, part 1 • Volume 179 • Number 3 • p671 to p676 whose contents are hereby incorporated by reference.

A further difficulty in the study of this problem is the relative rarity of serious fetal compromise, both due to its natural low incidence and the fact that the medical team will intervene to prevent its full development whenever there is an indication of it beginning. The difficulty inherent in studying a rare event has been addressed by substituting more commonly observed early new-born outcome characteristics that are related to permanent birth related neurological damage. Examples of these more commonly observed outcomes are low Apgar scores, (a 10 point measure of vigor at birth), or rates of caesarean section for fetal distress. A further extension of this concept is to use even simpler measures such as a scoring of the fetal heart rate record and placing it in various categories based on the cumulative score (Krebs, Fischer scores).

A deficiency of methods of the type described above is that the prognosis of babies with these outcomes e.g. low Apgar scores, caesarean section for fetal distress, low Fisher or low Krebs scores, is generally very good. These tests do not allow an adequate level of discrimination between babies who have poor prognosis and those with a good prognosis.

In the context of the above, there is a need in the industry to provide a method and device for classifying a condition of a fetus that alleviates at least in part problems associated with the existing methods.

SUMMARY OF THE INVENTION

In accordance with a first broad aspect, the invention provides a method suitable for monitoring the condition of a fetus. A signal indicative of a fetal heart rate is received and processed to derive data indicative of a degree of risk of developing a permanent neurological condition. The data indicative of the degree of risk of developing a permanent neurological condition indicates a likelihood that the condition of the fetus belongs to a class in a group of classes, each class in the group of classes being associated with a pre-defined fetal condition. The data indicative of the degree of risk of developing a permanent neurological condition is then released.

An advantage of the present invention is that the degree of risk of developing a permanent neurological condition can be more objectively diagnosed.

Another advantage of the present invention is that by providing a more objective pre-delivery diagnosis, a later assessment regarding the issue of whether severe neurological damage could have been prevented can be more objectively assessed. For instance, in lawsuits the presence of objective and reliable data will allow the actions of the health care team to be considered and defended in a court of law.

In accordance with a non-limiting implementation, a signal indicative of uterine activity is also received and processed with the signal indicative of the fetal heart rate to derive the data indicative of a degree of risk of developing a permanent neurological condition.

In accordance with a specific implementation, each class in the group of classes is characterised by the presence or absence of new-born encephalopathy and according to the arterial cord blood gas base deficit, herein referred to as base deficit (BD), being above or below a pre-determined level.

In a specific implementation, the group of classes includes four classes namely:
- a first class associated to a pre-determined fetal condition indicative of the presence of new-born encephalopathy and a base deficit measurement above a pre-determined level;
- a second class associated to a pre-determined fetal condition indicative of the presence of new-born encephalopathy and a base deficit measurement below a pre-determined level;
- a third class associated to a pre-determined fetal condition indicative of the absence of new-born encephalopathy and a base deficit measurement above a pre-determined level; and
- a fourth class associated to a pre-determined fetal condition indicative of the absence of new-born encephalopathy and a base deficit measurement below a pre-determined level.

Advantageously, the invention allows classifying the condition of a fetus such as to indicate the presence or absence of new-born encephalopathy and the base deficit level being above or below a pre-determined level. When the baby is a fetus in-utero, the base deficit and the presence or absence of newborn encephalopathy cannot be directly assessed. The invention makes use of the fetal heart rate signal to classify the condition of the fetus according to the above-described classes.

Several mathematical techniques as well as rule-based techniques can be used to characterise the association of fetal heart rate patterns to the classes. Alternatively, artificial neural networks can be used to characterise the associations between fetal heart rate patterns and the classes described above.

In accordance with a specific implementation, the signal indicative of the fetal heart rate is processed using a neural network to derive a degree of risk of developing a permanent neurological condition related to hypoxic injury. The neural network includes a plurality of inputs and a set of outputs, the outputs corresponding to respective classes in the group of classes. The neural network is adapted to release at each of the outputs a likelihood value associated to a respective class in the group of classes indicating the likelihood that the condition of the fetus belongs to a given class.

In a non-limiting implementation, the signal indicative of a fetal heart rate is processed to derive a plurality of feature measures. These feature measures are provided to the plurality of inputs of the neural network. The signal indicative of a fetal heart rate includes heart rate information collected over a certain period of time. The certain period of time may have any suitable duration. In a specific non-limiting example, the certain period of time is in excess of 1 hour. In another specific non-limiting example, the certain period of time is in excess of 2 hours. In another specific non-limiting example, the certain period of time is in excess of 3 hours. In yet another specific non-limiting example, the certain period of time is in excess of 4 hours.

In accordance with another broad aspect, the invention provides an apparatus for monitoring the condition of a fetus in accordance with the above-described method.

In accordance with yet another broad aspect, the invention provides a computer readable medium including a program element suitable for execution by a computing apparatus for monitoring the condition of a fetus in accordance with the above described method.

In accordance with another broad aspect, the invention provides a trained neural network for monitoring the condition of a fetus. The neural network comprises an input unit, a processing core and a set of outputs. The input unit is for receiving feature measures derived from a signal indicative of a fetal heart rate of a fetus. The set of outputs are associated to respective classes in a group of classes, each class in the group of classes being associated with a pre-defined fetal condition. The processing core processes the feature measures received at the input unit and releases at each output in the set of outputs data indicative of a likelihood that the condition of the fetus belongs to a respective class.

In accordance with a non-limiting implementation, the input unit also receives feature measures derived from a signal indicative of uterine activity.

In accordance with a specific implementation, each class in the group of classes is characterised by the presence or absence of new-born encephalopathy and according to the arterial cord blood gas base deficit, herein referred to as base deficit (BD), being above or below a pre-determined level. In a specific implementation, the group of classes includes the four classes described above.

In accordance with yet another broad aspect, the invention provides a computer readable medium including a program element suitable for execution by a computing apparatus for implementing the above described neural network.

In accordance with another broad aspect, the invention provides a method for training a neural network suitable for monitoring the condition of a fetus. The method includes receiving a plurality of records, each record comprising a first entry indicative of a fetal heart rate signal and a second entry indicative of a class selected from a group of classes, each class in the group of classes being indicative of a pre-defined fetal condition. The neural network is conditioned on the basis of the first and second entries of each record such as to enable the neural network, upon reception of a signal indicative of a fetal heart rate to derive a likelihood that the condition of the fetus belongs to a class in the group of classes.

In accordance with a specific implementation, each class in the group of classes is characterised by the presence or absence of new-born encephalopathy and according to the arterial cord blood gas base deficit, herein referred to as base deficit (BD), being above or below a pre-determined level. In a specific implementation, the group of classes includes the four classes described above.

In accordance with a specific implementation, the neural network assigns likelihood values to each class in the group of classes, at least in part on the basis of the signal indicative of a fetal heart rate. The neural network includes a plurality of inputs and a set of outputs, the outputs corresponding to respective classes in the group of classes. The signal indicative of a fetal heart rate is processed to derive a plurality of feature measures. The plurality of feature measures is then provided to the plurality of inputs of the neural network.

In accordance with another aspect, the invention provides a neural network conditioned on the basis of the above-described method.

In accordance with another broad aspect, the invention provides an apparatus suitable for monitoring the condition of a fetus. The apparatus includes an input, a feature extraction unit, a neural network module and an output. The input is for receiving a signal indicative of a fetal heart rate.

The feature extraction unit processes the signal indicative of the fetal heart rate to derive feature measures. The neural network module processes the feature measures to derive data indicative of a degree of risk of developing a permanent neurological condition. The data indicative of the degree of risk of developing a permanent neurological condition indicates a likelihood that the condition of the fetus belongs to a class in a group of classes, each class in the group of classes being associated with a pre-defined fetal condition. The output releases the data indicative of the degree of risk of developing a permanent neurological condition.

In accordance with a specific implementation, the feature extraction unit processes the fetal heart rate to identify a plurality of feature events. The feature extraction unit processes the plurality of feature events to generate a plurality of feature measures. The plurality of feature measures is then summarised to generate a compact representation of feature measures. The compact representation of feature measures is then release by the feature extraction unit for processing by the neural network module.

In a non-limiting implementation, the plurality of feature events includes at least some events selected from the set consisting of baseline, acceleration, deceleration and contraction events.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

In the accompanying drawings:

FIGS. 2a, 2b, 2c and 2d show alternative specific examples of the output of the fetal monitoring system shown in FIG. 1;

Other aspects and features of the present invention will become apparent to those ordinarily skilled in the art upon review of the following description of specific embodiments of the invention in conjunction with the accompanying figures.

DETAILED DESCRIPTION

Figure 1:
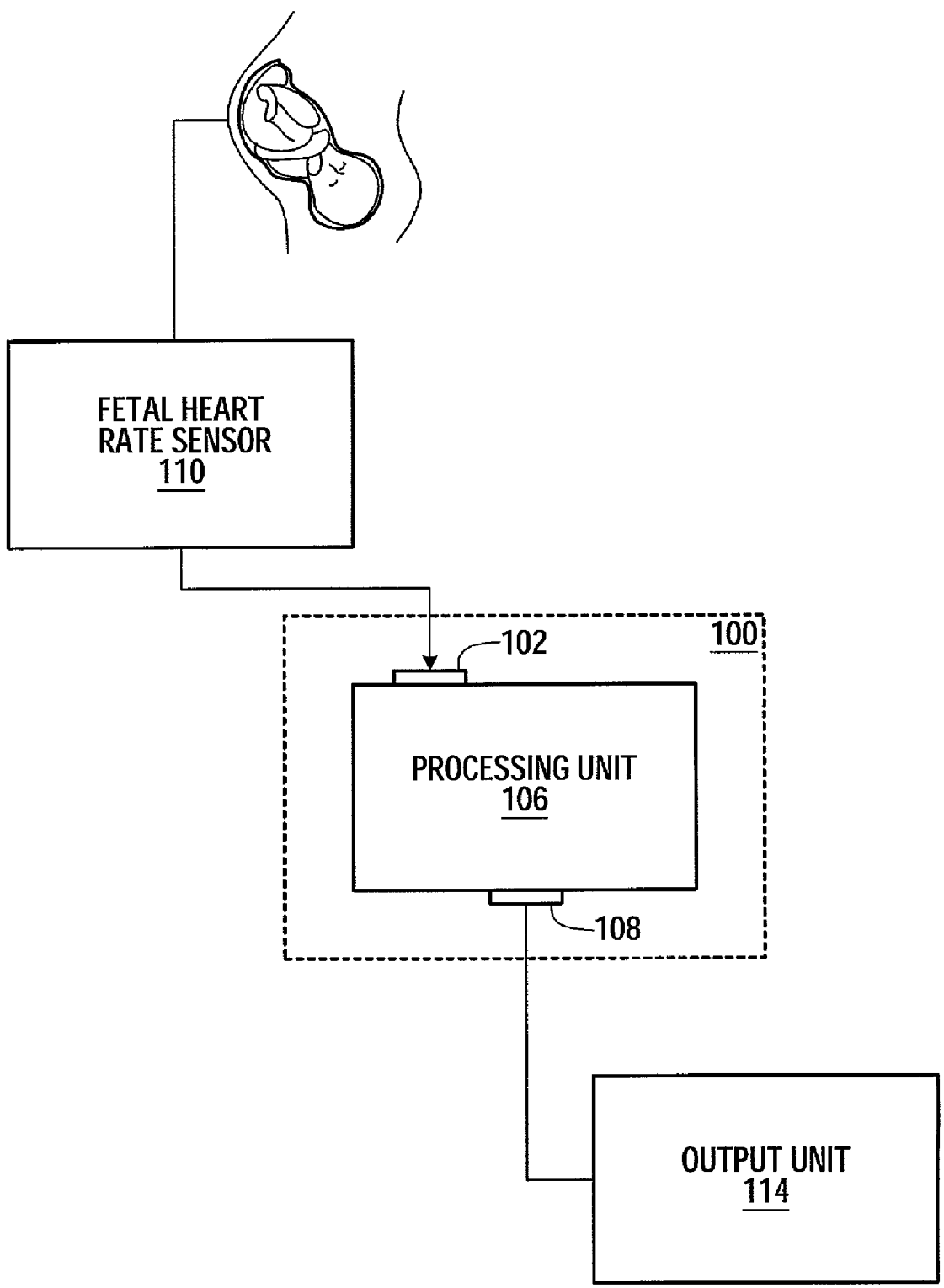
FIG. 1 shows a high level block diagram of a fetal monitoring system in accordance with a specific example of implementation of the present invention.

With reference to FIG. 1, there is shown a configuration of a fetal monitoring system comprising a fetal heart rate sensor 110, an apparatus suitable for monitoring the condition of a fetus 100 and an output unit 114.

The fetal heart rate sensor 110 is for detecting a fetal heart rate of a fetus in-utero, also referred to as a fetus in the womb. The fetal heart rate sensor 110 samples the fetal heart rate at a certain pre-determined frequency to generate the signal indicative of the fetal heart rate. Fetal heart rate sensors are well known in the art to which this invention pertains and any suitable sensor for detecting a fetal heart rate may be used without detracting from the spirit of the invention and as such will not be described further here.

In a non-limiting implementation, the fetal monitoring system includes a sensor (not shown) for monitoring uterine activity (TOCO). The sensor samples the contraction pattern at a certain pre-determined frequency to generate the signal indicative of uterine activity. Sensors for monitoring uterine activity are well known in the art to which this invention pertains and any suitable sensor may be used without detracting from the spirit of the invention and as such will not be described further here.

The signal indicative of the fetal heart rate and the signal indicative of uterine activity may be processed jointly or separately by processing unit 100 to derive data indicative of a degree of risk of developing a permanent neurological condition. For the purpose of simplicity and conciseness, the processing of the signal indicative of the fetal heart rate by apparatus 100 is described in detail herein below. It will be readily appreciated that similar processing may be applied to the signal indicative of uterine activity without detracting from the spirit of the invention.

The apparatus suitable for monitoring the condition of a fetus 100 includes an input 102, a processing unit 106 and an output 108. The input 102 receives the signal indicative of the fetal heart rate from the fetal heart rate sensor 110. The processing unit 106 processes the signal received at input 102 to derive data indicative of a degree of risk of developing a permanent neurological condition. More specifically, the processing 106 unit derives a likelihood that the condition of the fetus belongs to a class in a group of classes, each class in the group of classes being associated with a pre-defined fetal condition. The likelihood may be in the form of a probability value, a ranking or any other value that allows ordering the classes on the basis of the confidence level that the condition of the fetus belong to the class.

In accordance with a specific implementation, each class in the group of classes is characterised by the presence or absence of new-born encephalopathy and according to the arterial cord blood gas base deficit, herein referred to as base deficit (BD), being above or below a pre-determined level. The pre-determined level of base deficit is selected such that infants having a base deficit level above the pre-determined level are associated to a higher degree of risk of developing cerebral palsy than children below the pre-determine level. In a non-limiting specific implementation, the pre-determined level of base deficit measurement is about 12 mmol/L. Alternatively, the pre-determined level of base deficit may be different for a fetal condition characterised by the presence of new-born encephalopathy and a foetal condition characterised by the absence of new-born encephalopathy. In a non-limiting specific implementation, the pre-determined level of base deficit measurement is about 12 mmol/L when the foetal condition is characterised by the presence of new-born encephalopathy and 8 mmol/L when the foetal condition is characterised by the absence of new-born encephalopathy. It will be appreciated that other suitable pre-determined levels of base deficit may be used without detracting from the spirit of the invention.

Generally speaking, neonatal encephalopathy is a collection of neurologic signs typically including hypotonia, hypertonia, respiratory or feeding difficulty of central origin, seizures, coma. According to the American College of Obstetrics and Gynecology and the Society of Obstetricians and Gynecologists of Canada SOGC clinical guidelines, the characteristics of the newborn response to asphyxia of such a degree as to be likely to cause permanent harm include neonatal encephalopathy. The measure of base deficit is typically measured in the arterial blood of the umbilical cord. This is a measure of metabolic acidosis and is considered to be a direct consequence of fetal tissue oxygen deprivation. The level of base deficit measurement indicates whether the baby was exposed to substantial oxygen deprivation. Increasing degrees of metabolic acidosis with arterial cord base deficit levels over 12 mmol/L are highly correlated with neurological deficits later in their lives. For additional information regarding the above, the reader is invited to consult Low J. A., *The role of blood gas and acid-base assessment in the diagnosis of intrapartum fetal asphyxia*, Am J Obstet Genecol, 1988; 159:1234–40 and Low J. A. et al., *Motor and cognitive deficits after intrapartum asphyxia in the mature fetus*, Am J Obstet Gynecol. 1988 February; 158(2):356–61. The content of the above documents is hereby incorporated by reference.

Advantageously, by providing a classification of the condition of the fetus according to the measure of base deficit and the presence or absence of neonatal encephalopathy, a useful indication of the degree of risk of developing a permanent neurological condition related to hypoxic injury can be obtained.

In a specific implementation, the group of classes includes four classes namely:
- a first class, herein referred to as Class A, associated to a pre-determined fetal condition indicative of the presence of new-born encephalopathy and a base deficit measurement above a pre-determined level;
- a second class, herein referred to as Class B, associated to a pre-determined fetal condition indicative of the presence of new-born encephalopathy and a base deficit measurement below a pre-determined level;
- a third class, herein referred to as Class C, associated to a pre-determined fetal condition indicative of the absence of new-born encephalopathy and a base deficit measurement above a pre-determined level; and
- a fourth class, herein referred to as Class D, associated to a pre-determined fetal condition indicative of the absence of new-born encephalopathy and a base deficit measurement below a pre-determined level.

When the baby is a fetus in-utero, the base deficit and the presence or absence of newborn encephalopathy cannot be directly assessed. The processing unit 106 makes use of the fetal heart rate signal received from the fetal heart rate sensor 110 to classify the condition of the fetus according to the above described classes.

Advantageously, the above described classification provides intermediate risk classes where it is likely that intervention would prevent the baby from deteriorating into the category associated with a high likelihood of development of cerebral palsy. For example, a high likelihood of the condition of the fetus being classified in class A indicates to the physician or other health care professional that the fetus is in a high risk category for developing cerebral palsy. Alternatively, a high likelihood of the condition of the fetus being classified in classes B or C indicates to the physician or other health care professional that the condition fetus is in an intermediate risk category for developing cerebral palsy and that intervention may prevent the fetus from deteriorating in to a class having a greater risk for developing cerebral palsy such as class A. Finally, a high likelihood of the condition of the fetus being classified in class D indicates to the physician or other health care professional that the condition fetus is in a low risk category for developing cerebral palsy and the intervention on this basis may not be necessary.

The processing unit 106 releases at its output 108 data indicative of the degree of risk of developing a permanent neurological condition. In a first non-limiting example, the data is in the form of confidence levels associated to the respective classes in the group of classes indicating the likelihood of the condition of the fetus belonging to each class. In a second non-limiting example, the data includes an identifier associated to the class to which the condition of the fetus is most likely to belong.

The output unit 114 receives the data indicative of the degree of risk of developing a permanent neurological condition generated by the processing unit 106 and provides it to the physician or other health care professional in a visual and/or audio format. The output unit 114 may be in the form of a display screen, a paper print out or any other suitable device for conveying to the physician or other health care professional the data indicative of the degree of risk of developing a permanent neurological condition. In a first non-limiting implementation, as shown in FIG. 2a, the output unit 114 provides each class and its associated likelihood to the physician or other health care professional. In a second non-limiting example, as shown in FIG. 2b, the output unit 114 provides the class to which the condition of the fetus is most likely to belong and optionally associated likelihood to the physician or other health care professional. In a third non-limiting example, as shown in FIG. 2c, the output unit 114 provides a description of the condition of the fetus derived on the basis of the class the fetus is most likely to belong. The output unit 114 may provide the physician or other health care professional with data indicative of the degree of risk of developing a permanent neurological condition in a plurality of other suitable fashions, which will be readily apparent to the person skilled in the art in light of this description.

Figure 2D:
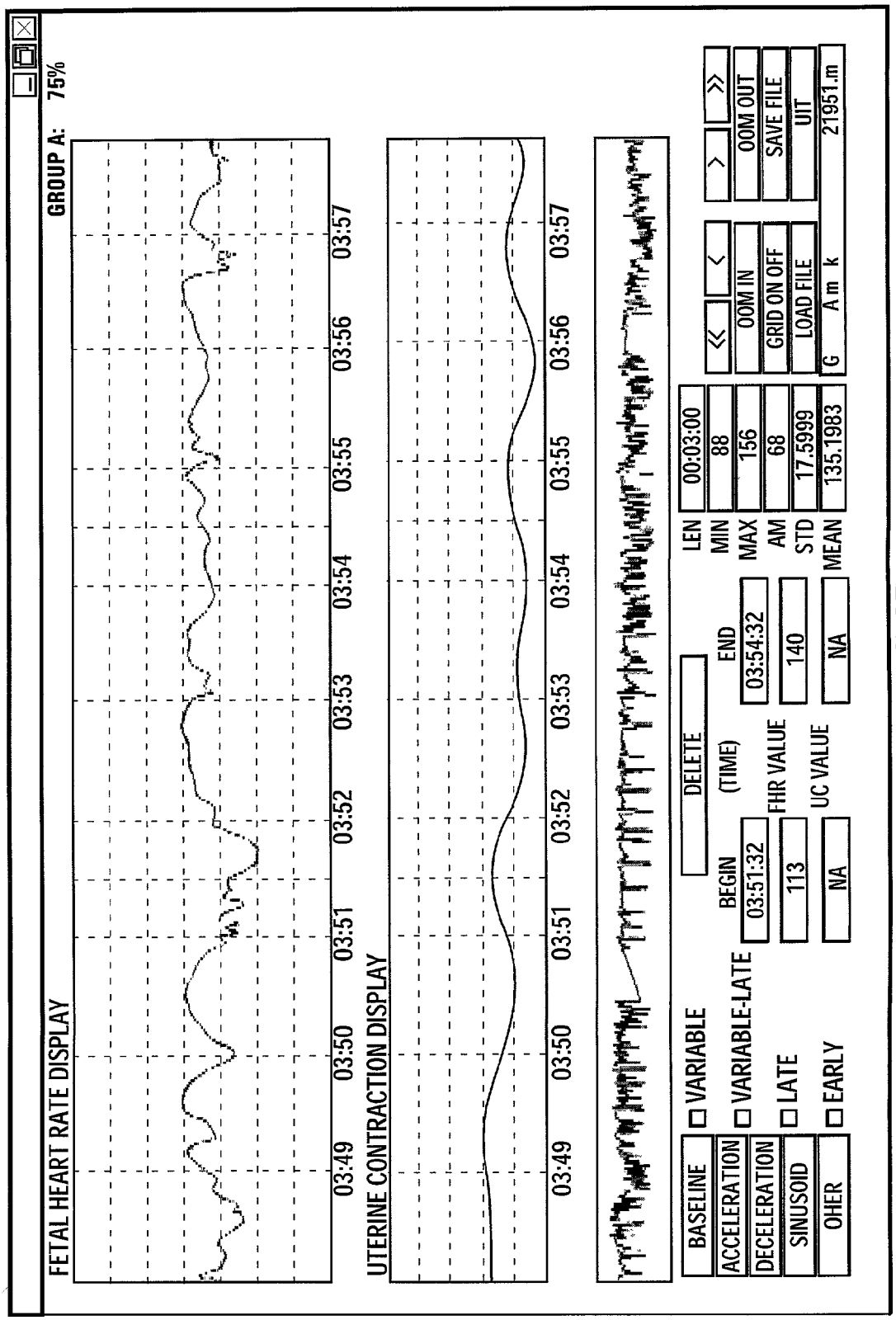

As shown in FIG. 2d, the output unit 114 may also display fetal heart rate patterns and other information in addition to the data indicative of the degree of risk of developing a permanent neurological condition.

The manner in which the processing unit 106 processes the fetal heart rate signal to classify the condition of the fetus in-utero is described in greater detail herein below.

Processing Unit 106

The processing unit 106 (shown in FIG. 1) implements an expert system to derive the degree of risk of developing a permanent neurological condition associated to the fetus. The expert system implemented by the processing unit 106 may be rule-based where the association of fetal heart rate and a class are expressed mathematically or through a logical/algorithmic association. Alternatively, trained artificial neural networks can be used to characterise the associations between fetal heart rate patterns and the classes described above. Advantageously, the use of a neural network allows modelling complex interrelated non-linear relationships between the fetal heart rate patterns and the above-described classes. In yet another alternative, the processing unit 106 makes use of a combination of an artificial neural network and a rule-based expert system.

Figure 3:
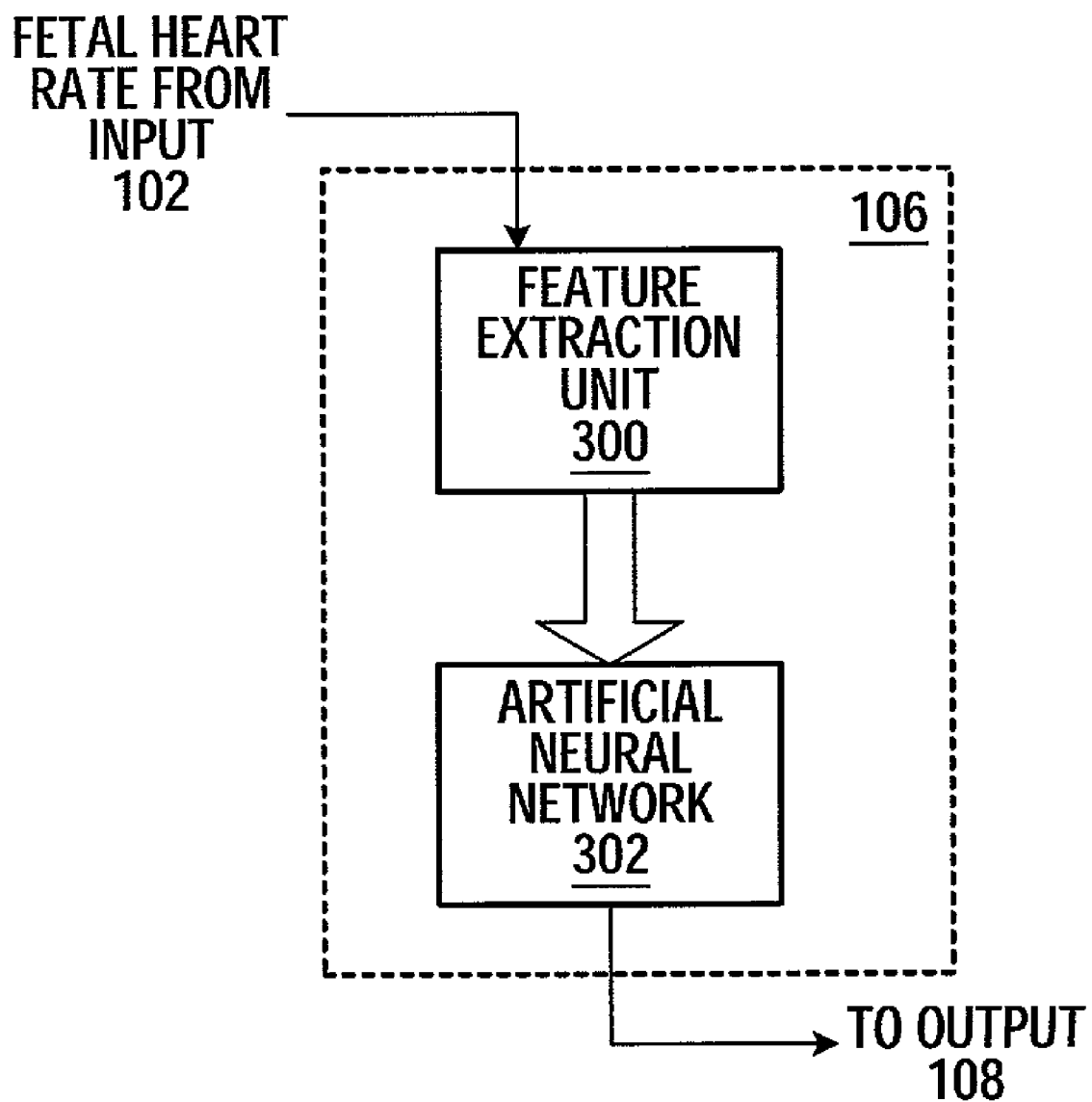
FIG. 3 shows a block diagram of a processing unit operative to derive a degree of risk of developing a permanent neurological condition in accordance with a specific example of implementation of the present invention.

As shown in FIG. 3, the processing unit 106 includes a feature extraction unit 300 and a trained artificial neural network module 302.

The feature extraction unit 300 processes the signal indicative of a fetal heart rate received at input 102 over a certain period of time to derive a plurality of feature measures characterising the signal indicative of the fetal heart rate.

The trained artificial neural network module 302 includes a plurality of inputs and a set of outputs, where the outputs correspond to respective classes in the group of classes. The neural network module 302 is adapted to process the plurality of feature measures received at its inputs to release at each of the outputs a likelihood value associated to a respective class.

The feature extraction unit 300 and the neural network module 302 are described in greater detail herein below.

Feature Extraction Unit 300

The feature extraction unit 300 processes the fetal heart rate signal over a certain period of time to generate a plurality of feature measures. The certain period of time may have any suitable duration. In a specific non-limiting example, the certain period of time is in excess of 1 hour. In another specific non-limiting example, the certain period of time is in excess of 2 hours. In another specific non-limiting example, the certain period of time is in excess of 3 hours. In yet another specific non-limiting example, the certain period of time is in excess of 4 hours. The time period used by the feature extraction unit has the same duration as the fetal heart rate signal on which the neural network was trained. Where the fetal heart rate signal, which is being processed, has a duration that is different from the duration of the signal on which the neural network was trained, extrapolation/truncation and compression methods may be used to expand or shorten the duration of the fetal heart rate signal. The feature extraction unit 300 releases the plurality of feature measures and provides them to the artificial trained neural network module 302.

Figure 5:
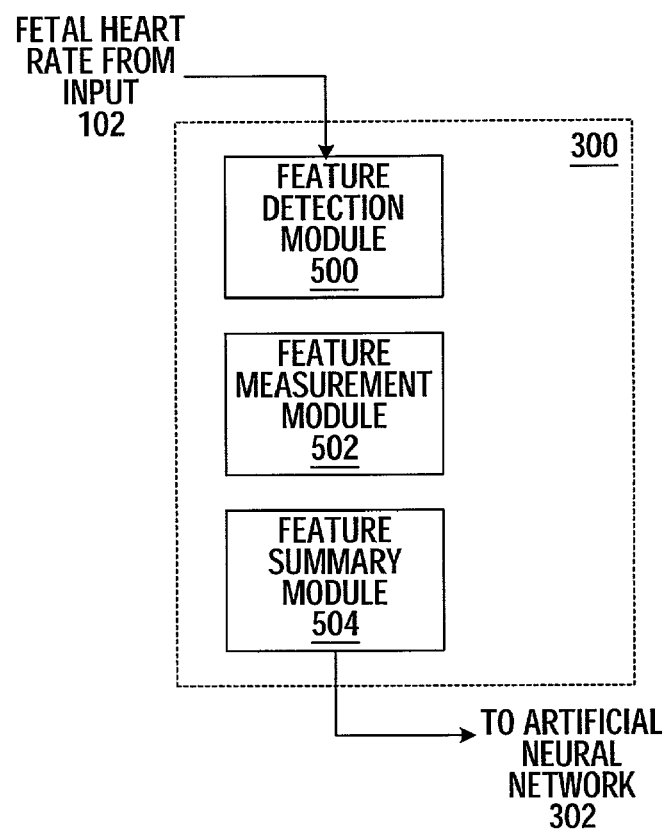
FIG. 5 is a block diagram of a feature extraction unit implemented by the processing unit depicted in FIG. 3 in accordance with a non-limiting example of implementation of the invention.

The feature extraction unit 300 is shown in greater detail in FIG. 5 and includes three functional modules namely a feature detection module 500, a feature measurement module 502 and a feature summary module 504.

Figure 8:
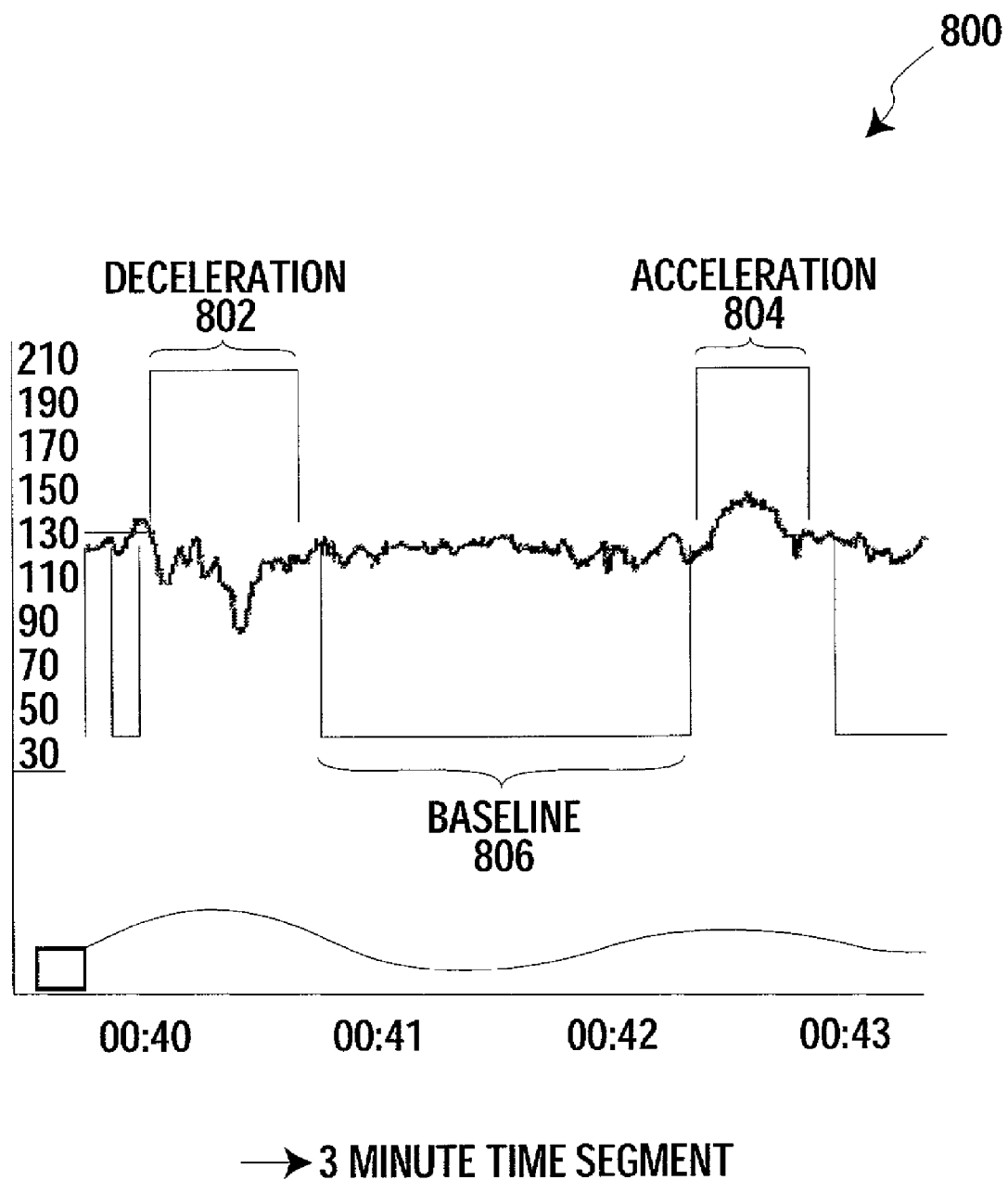
FIG. 8 shows a portion of a simplified fetal heart rate signal with labelled feature events in accordance with a non-limiting example of implementation of the invention.

The feature detection module 500 processes the fetal heart rate signal and performs a time-domain segmentation of the fetal heart rate signal to locate feature events of interest. In a non-limiting example of implementation, the feature detection module 500 detects features events including without being limited to baseline, deceleration, acceleration and contraction feature events. Any suitable method for detecting baseline, deceleration, acceleration and contraction events may be used here without detracting from the spirit of the invention. For additional information, the reader is invited to refer to Mantel R, Van Geijn H P, Caron F J M, Swartjes J M, Van Woerden E E, Jongsma H W: Computer analysis of antepartum fetal heart rate: 1. baseline determination. 2. detection of accelerations and decelerations. Int J Biomed Comput 25, 261(1990). The content of the above document is hereby incorporated by reference. A simplified representation of a portion of a fetal heart rate signal where the baseline, deceleration, acceleration events are labelled is shown in FIG. 8. FIG. 8 shows a portion 800 of a fetal heart signal having a duration of about 3-minutes. The portion 800 has been segmented by the feature detection module 500 such as to indicate a deceleration feature event 802, a baseline feature event 806 and an acceleration feature event 804. For each feature event, a determination of its temporal location within the fetal heart rate signal, namely the beginning and ending time of the feature event, is made. Although FIG. 8 shows the time-domain segmentation performed by the feature detection module 500 for a 3-minute segment, the above process is performed for the entire fetal heart rate signal being processed. The feature detection module 500 releases a list of feature events with their beginning and ending times.

The feature measurement module 502 receives the list of feature events with their beginning and ending times from the feature detection module 500. For each feature event, measures are generated describing characteristics of the feature event. In a non-limiting specific implementation, for a baseline feature event, feature measures describing the mean, frequency, length, variability and sinusoidal pattern of the baseline feature event are calculated. For a deceleration or acceleration feature event, feature measures describing the mean, frequency, length, variability and area of the deceleration or acceleration feature event are calculated. For a contraction feature event, feature measures describing the frequency and deceleration recovery time of the contraction feature event are calculated. The time sequence of certain feature events with respect to other feature events, which can be of clinical significance (e.g. deceleration recovery time following contraction), may be included in the feature measures. The table below illustrates a non-limiting example of various feature measures used for certain feature events. It will be readily apparent to the person skilled in the art that other feature measures may be used in addition to the feature measures identified below and certain feature measure may be omitted without detracting from the spirit of the invention.

TABLE 1

Example of feature measures

| Baseline | Deceleration | Acceleration | Contraction |
|---|---|---|---|
| Mean | Mean | Mean | Deceleration recovery time |
| Frequency | Frequency | Frequency | Frequency |
| Length | Length | Length | |
| Variability | Variability | Variability | |
| Sinusoidal pattern | Area | Area | |

The computation of the various feature measures may be effected using any suitable technique. Such techniques are well known in the art of signal processing and as such will not be described further here. Generally, where the fetal heart rate signal is processed over a long period of time, several thousands of features measures are obtained.

Figure 9A:
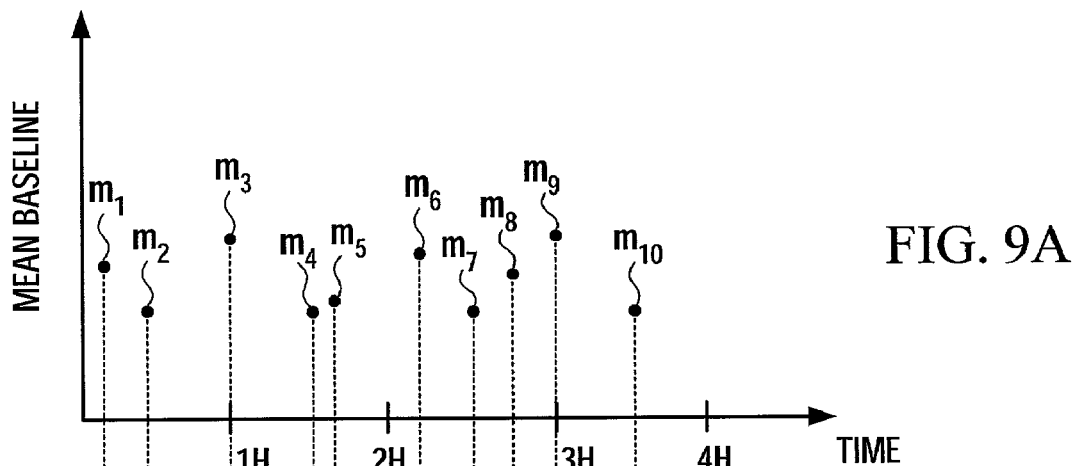
FIGS. 9a, 9b, 9c and 9d are graphs showing feature measures generated by the feature extraction unit in accordance with a non-limiting example of implementation of the present invention.

The feature measurement module 502 releases a plurality of sets of feature measures, each set of feature measures includes feature measures describing a given characteristic of a feature event. For example, a first set of feature measures will include all the features measures for the mean values of baseline feature events. A second set of feature measures will include all the features measures for the frequency values of baseline feature events. A third set of feature measures will include all the features measures for the mean values of acceleration feature events and so on. Generally speaking, the sets of feature measures characterise feature events that are irregularly spaced in time. FIG. 9a shows in simplified form the set of feature measures for the baseline mean values over a 4-hour time period. As shown, the fourteen feature measures labelled $M_1$ to $M_{14}$ are irregularly spaced in the time domain.

The feature summary module 504 receives the sets of feature measures from the feature measurement module 502. For each set of feature measure, the feature summary module 504 processes the feature measures in the set to obtained a set of feature measures which is compact and regularly spaced in the time domain.

Figure 9B:
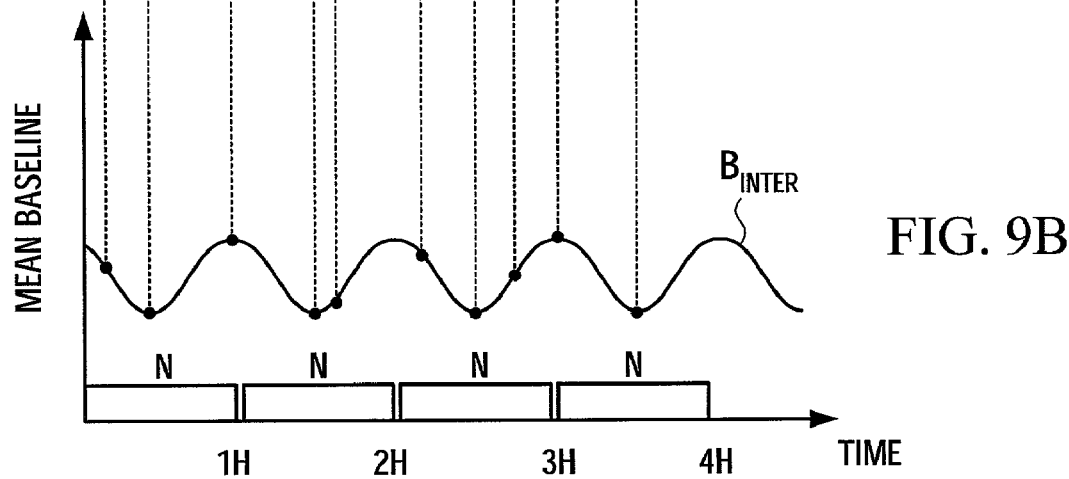

In a non-limiting example, this process is effected in two steps. The first step involves interpolating the feature measures in each set onto a sampling grid to generate a plurality of feature measures where the sampling grid has a certain frequency. Any suitable type of interpolation may be used including linear, spline or cubic interpolation. In a specific non-limiting implementation, the sampling grid has a frequency equal to the frequency of the fetal heart rate signal. FIG. 9b shows in simplified form the set of feature measures for the baseline mean over a 4-hour time period interpolated at the frequency of the fetal heart rate signal. The signal depicted is labelled $b_{INTER}$ and forms the interpolated set of feature measures for the mean values of baseline feature events.

Figure 9C:
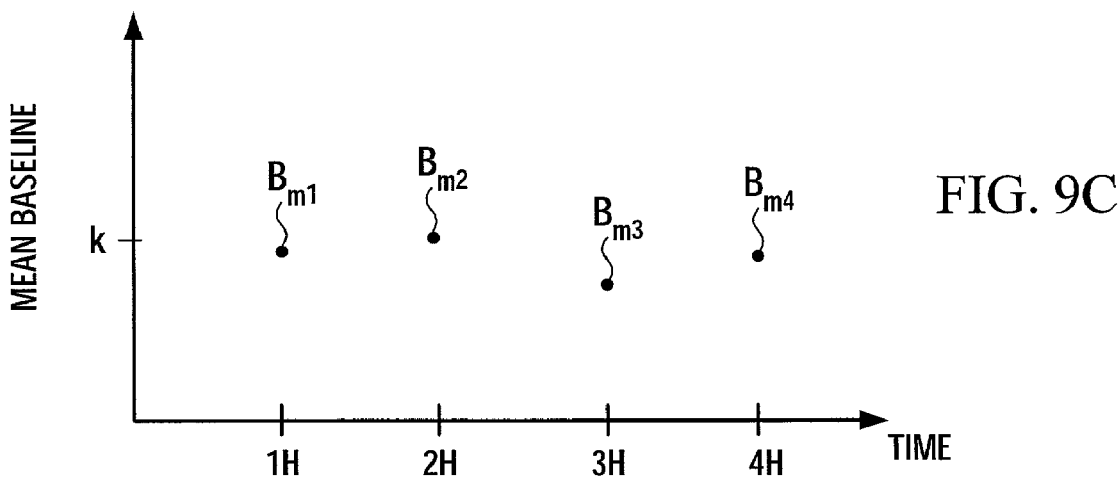

Optionally, following the interpolation of the feature measures and in order to reduce the amount of data to be processed by the neural network module 302 (shown in FIG. 3), the interpolated set of feature measures $b_{INTER}$ is decimated at a desired sampling rate by a low-pass filter to generate a compact representation of the set of feature measures. The desired sampling rate may be different for each set of feature measures. For example, feature measures that change more rapidly can be given a time resolution that adequately describes them. For example, the features measures for the variability values of baseline feature events may be sampled to get a value at each 60 minute interval while the features measures for the mean values of baseline feature events may be sampled to get a value at each 15 minute interval. FIG. 9c shows in simplified form the set of feature measures for the baseline mean over a 4-hour time period decimated to obtain a sample at every hour. As shown, the baseline feature measures for the mean are summarised as four feature measures labelled $B_{m1}$, $B_{m2}$, $B_{m3}$ and $B_{m4}$ respectively in FIG. 9c. Feature measures labelled $B_{m1}$, $B_{m2}$, $B_{m3}$ and $B_{m4}$ form a compact representation of the set of feature measures for the mean values of baseline feature events for the four-hour time period.

Figure 9D:
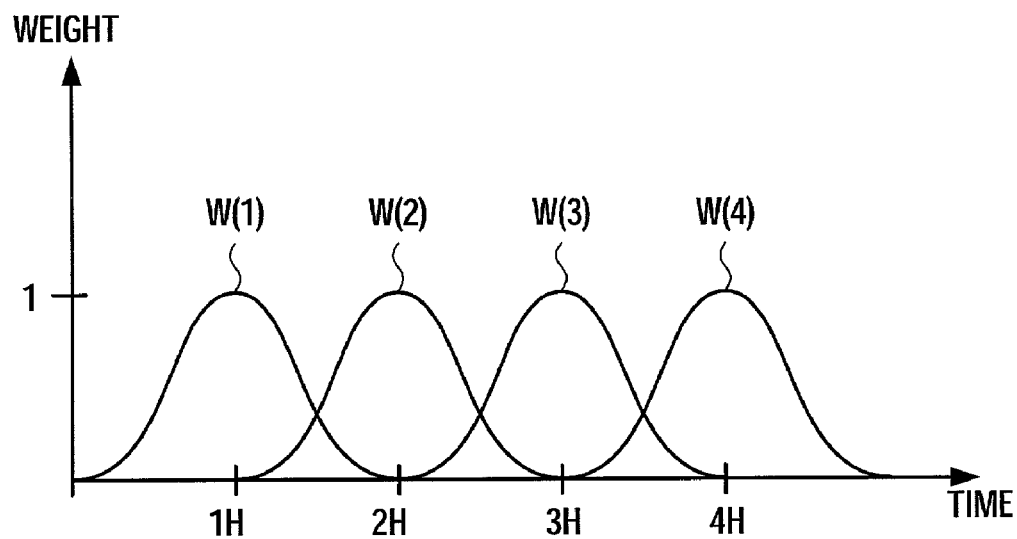

Many decimation techniques for reducing the number of feature measures in the interpolated set of feature measures $b_{INTER}$ may be used here for reducing the number of feature measures without detracting from the spirit of the invention. In a non-limiting implementation, a weighted average of the feature measures in the interpolated set of feature measures $b_{INTER}$ is used to obtain the feature measure value sampled at the decimated frequency. FIG. 9d illustrated a set of weighting windows applied to the interpolated signal $b_{INTER}$ shown in FIG. 9b to obtain the samples of FIG. 9c. In FIG. 9d, the weighting windows are labelled w[1], w[2], w[3] and w[4] and are associated to samples $B_{m1}$, $B_{m2}$, $B_{m3}$ and $B_{m4}$ respectively. Each weighting windows w[k] is selected such as to weigh more heavily feature measures in the interpolated set of feature measures $b_{INTER}$ occurring closer to sample $B_{mk}$ and to weigh less heavily feature measures in the interpolated set of feature measures $b_{INTER}$ occurring further sample $B_{mk}$. Mathematically, the computation of samples $B_{m1}$, $B_{m2}$, $B_{m3}$ and $B_{m4}$ can be expressed as follows:

$$B_{m1} = \frac{1}{2N} \sum_{i=0}^{N-1} w[1]_i * b_{INTER}[i]$$  Equation 1

$$B_{m2} = \frac{1}{2N} \sum_{i=N}^{2N-1} w[2]_i * b_{INTER}[i]$$

$$B_{m3} = \frac{1}{2N} \sum_{i=2N}^{3N-1} w[3]_i * b_{INTER}[i]$$

$$B_{m4} = \frac{1}{2N} \sum_{i=3N}^{4N-1} w[4]_i * b_{INTER}[i]$$

where N is the number of features measures at the interpolated frequency between the desired samples of the compact representation; w[k] is the weighting window associated to sample $B_{mk}$; and $b_{INTER}[k]$ is the kth feature measure the set of feature measures $b_{INTER}$.

In an alternative form, let be signal $b_{INTER}(n)$ include M samples (in the example shown in the figures M=4N). For the purpose of simplicity, we set $b_{INTER}(n)$ to zero outside the area of interest. Mathematically, this can be expressed as follows:

$b_{INTER}(n) = b_{INTER}(n)$ for $0 \leq n < M$ $b_{INTER}(n) = 0$ for $n < 0$ and $n \geq M$ Let v(n) be the output of a low-pass decimation filter (or "weighting function") w(n) where:

$$v(n) = \sum_{k=-\infty}^{\infty} b_{INTER}(k) w(n-k), \quad 0 \leq n < M$$

In a first non-limiting implementation, the compact representation of the set of feature measures is a regularly sampled signal (e.g. samples once per hour). The output signal is downsampled by a factor D. The output is every $D^{th}$ sample of v(n) and can be expressed as follows:

$$y(m) = v(mD), \quad 0 \leq m < P, \text{ where } P = \frac{M}{D}$$
$$= \sum_{k=-\infty}^{\infty} b_{INTER}(k) w(mD - k)$$

where y(m) is the mth output sample of the compact representation of the set of feature measures.

Figure 11B:
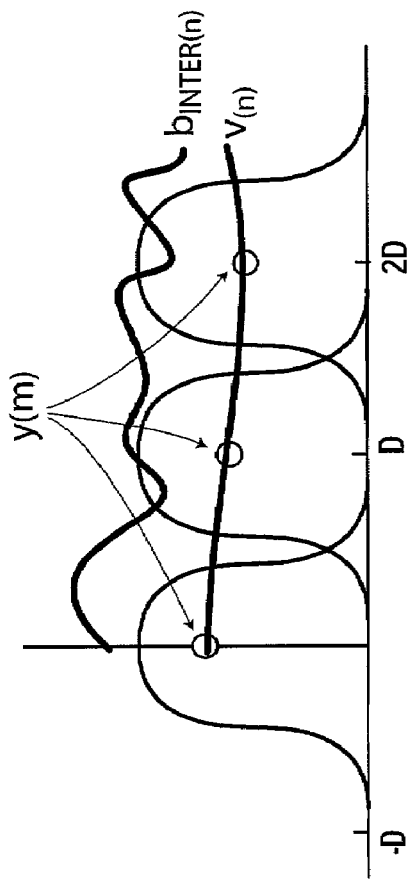
FIGS. 11a, 11b, 11c and 11d are graphs showing weighting windows for use in the decimation of sets of feature measures in accordance with non-limiting examples of implementation of the present invention.
Figure 11A:
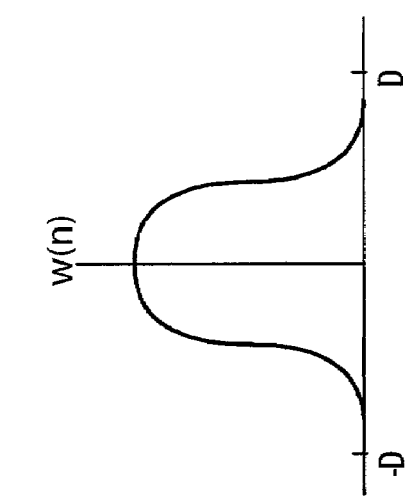

A non-limiting example of the signal v(m) is shown in FIG. 11b). The weighting function w(n), shown in FIG. 11a), is defined as:

$$w(n) = \frac{\overline{w}(n)}{\sum_{i=-D}^{D} \overline{w}(n)}$$

where $\overline{w}(n)$ is a raised cosine of limited extent:

$$\overline{w}(n) = 1 + \cos\left[\frac{(n-1)\pi}{D-1}\right], \quad -D \le n \le D$$
$$= 0, \quad |n| > D$$

and the denominator of w(n) is a normalizing factor.

Alternatively, the compact representation of the set of feature measures is a signal sampled with irregularly spaced samples. Advantageously, sampling with irregular intervals allows higher sampling during time intervals considered most information-critical (e.g. the last hour of labour) than during intervals considered to be less information-critical.

Figure 11D:
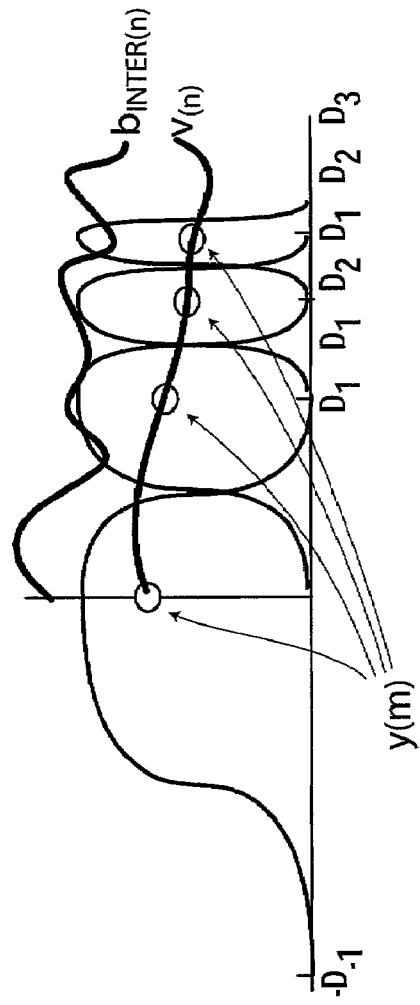
Figure 11C:
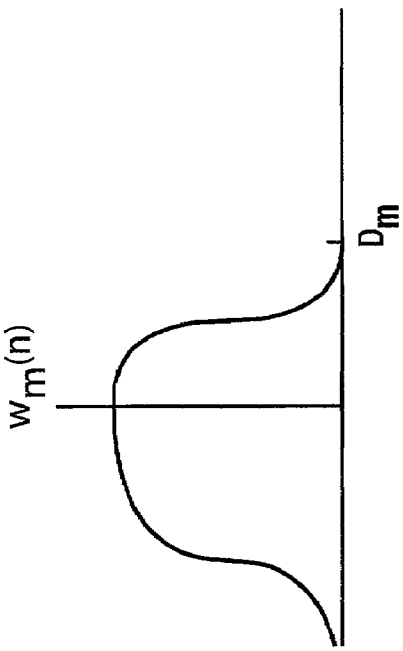

In a non-limiting implementation, a local weighting function $w_m(n)$, of the type shown in FIG. 11c), is applied at each sample of $b_{INTER}$. For example, if the sample spacing before and after sample m are $D_{m-1}$ and $D_m$ respectively, the weighting function before normalization can be expressed as follows:

$$\overline{w}_m(n) = 0, \quad n < -D_{m-1}$$
$$= 1 + \cos\left[\frac{(n-1)\pi}{D_{m-1}-1}\right], \quad -D_{m-1} \le n < 0$$
$$= 1 + \cos\left[\frac{(n-1)\pi}{D_m-1}\right], \quad 0 \le n \le D_m$$
$$= 0, \quad n > D_m$$

The output of the low-pass decimating filter, an example of which is shown in FIG. 11d), can be expressed in a mathematical format as follows:

$$v(n) = \sum_{k=-\infty}^{\infty} b_{INTER}(k) w_m(n-k), \quad 0 \le n < M$$

and the downsampled output signal is:

$$y(m) = v[i(m)]$$
$$= \sum_{k=-\infty}^{\infty} b_{INTER}(k) w_m(i(m)-k), \quad 0 \le m < P$$

where i(m) is the set of P indices into v(n) of the irregularly spaced sample points.

It will be appreciated that other methods for decimating signal $b_{INTER}$ may be used without detracting from the spirit of the invention.

For each set of feature measures, the above describe process of interpolation and decimation is effected by the feature summary module 504. The feature summary module 504 releases for each set of feature measures, the compact representation of the set of feature measures for processing by the neural network module 302 (shown in FIG. 3). Advantageously, by interpolating and decimating each set of feature measures, the feature summary module 502 presents feature measures to the neural network in a compact but representative fashion.

Artificial Trained Neural Network 302

Figure 4:
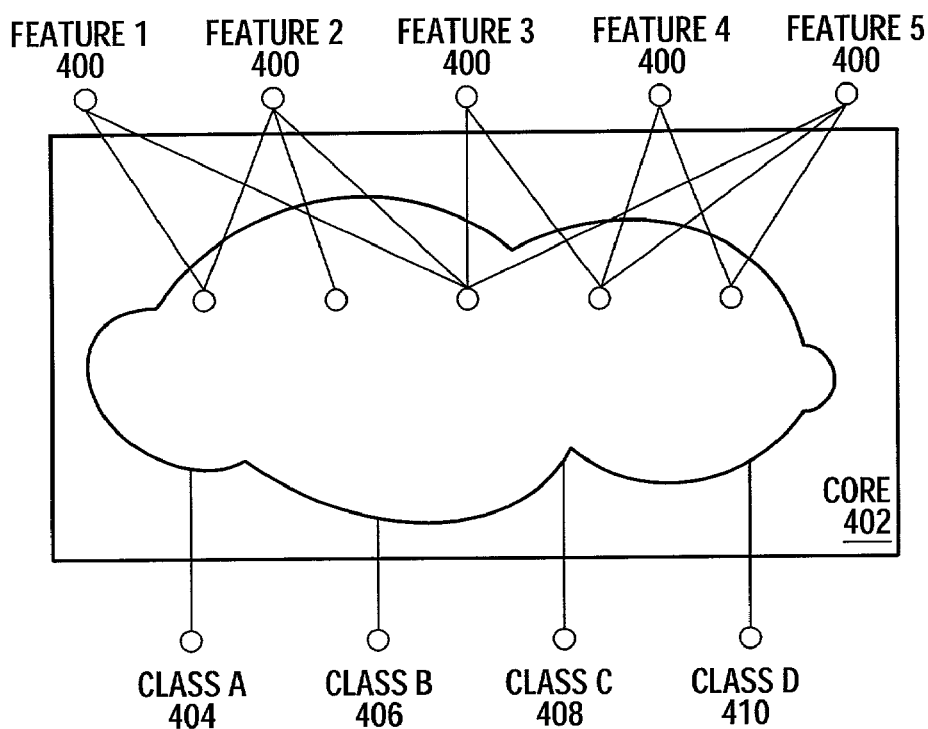
FIG. 4 shows a high level conceptual block diagram of a neural network implemented by the processing unit depicted in FIG. 3 in accordance with a non-limiting example of implementation of the invention.

A functional representation of the trained neural network module 302 is shown in FIG. 4 of drawings. As depicted, the trained neural network 302 includes an input unit 400, a processing core 402 and a set of outputs 404 406 408 410. The input unit 400 includes a plurality of inputs for receiving respective feature measures received from the feature extraction unit 300 (shown in FIG. 3).

Each output in the set of outputs 404 406 408 410 is associated to a respective class in the group of classes described above. In the non-limiting representation depicted in FIG. 4, output 404 is associated to class A, output 406 is associated to class B, output 408 is associated to class C and output 410 is associated to class D. The processing core 402 processes the feature measures received at the input unit 400 to release at each output data indicative of a likelihood that the condition of the fetus belongs to a respective class. In the non-limiting specific implementation, the neural network module 302 includes a multilayer perceptron (MLP) network trained by back propagation. The training of the artificial neural network is described herein below.

THE TRAINING PROCESS FOR THE ARTIFICIAL NEURAL NETWORK

Generally speaking, a neural network is a mathematical process capable of performing a large number of "experiments" based on observations to determine or "learn" the best way of mathematically representing the association between a given set of observations and an outcome. The neural network determines this association by processing a "training set" of data where it is given observations associated to respective actual outcomes in a set of pre-defined outcomes. The neural network is conditioned such that when the given observations are applied to its inputs, the corresponding actual outcome is released at the outputs. Conditioning a neural network in the basis of observations associated to respective actual pre-defined outcomes is known in the art and as such will not be described in further detail here. Once the neural network has been conditioned on the basis of the training set, when new observations are applied to the inputs of the neural network, likelihood values are released associated to the outcomes in the set of pre-defined outcomes indicating likelihood values that the new observations are associated to each pre-defined outcome. In this specific implementation, the observations are derived from fetal heart rate signals and are the feature measures and the set of pre-defined outcomes are the four classes (Class A; Class B; Class C and Class D) determined in the basis of the base deficit level and the presence or absence of neonatal encephalopathy.

Figure 6:
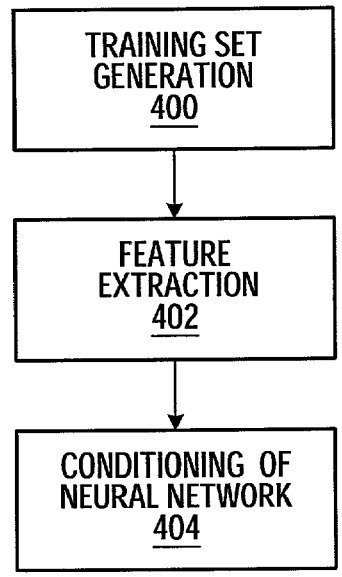
FIG. 6 is a flow diagram of a process for generating a trained neural network of the type depicted in FIG. 4 in accordance with a non-limiting example of implementation of the invention.

The training of the artificial neural network 302 is described herein below with reference to FIG. 6 of the drawings. The training process can be divided into three distinct steps namely training set generation 600, feature extraction 602 and conditioning of the neural network 604.

In the training set generation step 600, a pool of baby health profiles including a plurality of entries is processed. Each entry in the pool corresponds to a respective baby and describes a health profile associated to the baby including a fetal heart rate signal, a base deficit measure and data indicating the presence/absence of neonatal encephalopathy.

Typically, the base deficit is measured in a newborn blood sample, which usually taken from the umbilical cord just after the cord is cut. This is a measure of metabolic acidosis and is considered to be a consequence of fetal tissue oxygen deprivation. The base deficit measures the total concentration of blood buffer base in units of equivalents/L. The presence/absence of neonatal encephalopathy is a clinical assessment based on the presence of certain criteria well known in the field of obstetrics and as such will not be described in further detail here. For additional information on this topic, the reader is invited to refer to Sarnat, H B. & Sarnat, M S. Neonatal encephalopathy following fetal distress. Arch Neurol 1976; 33: 696–705 and Badawi, N., Kurinczuk, J J., Keogh, J M., Alessandri, L M., O'Sullivan, F., & Burton, P R. Antepartum risk factors for newborn encephalopathy: the Western Australian case-control study. BMJ 1998; 317: 15491553. The content of the above documents is hereby incorporated by reference.

Figure 7:
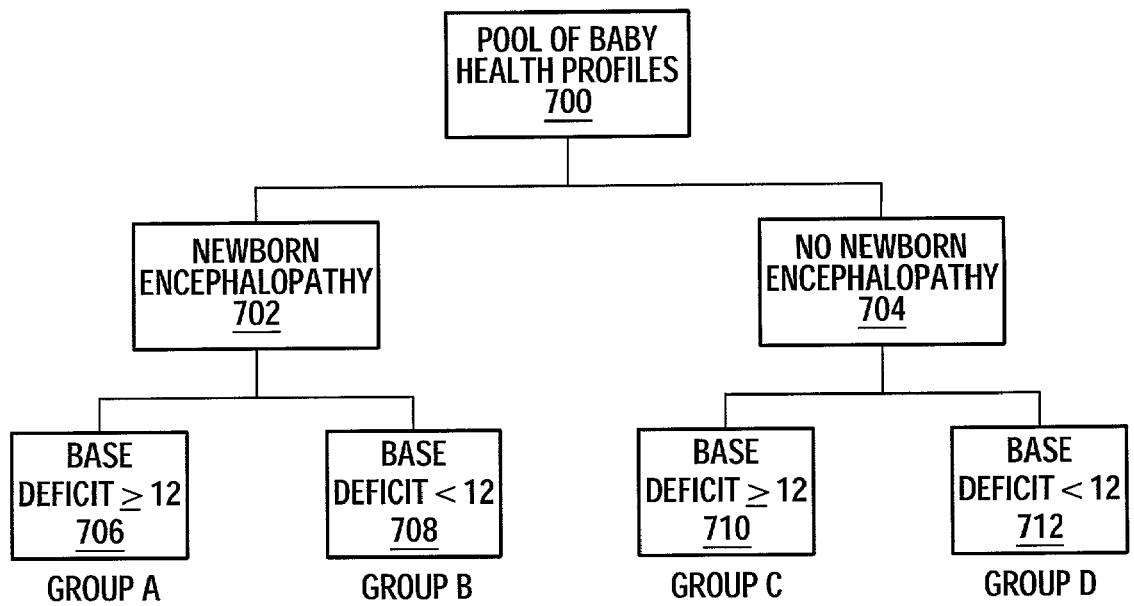
FIG. 7 is a block diagram depicted the classification scheme of a fetal condition on the basis of the presence/absence of neonatal encephalopathy and the base deficit level in accordance with a non-limiting example of implementation of the invention.

The presence of presence/absence of neonatal encephalopathy and the base deficit in each entry are used to classify the baby's condition into one of four classes. The classification scheme is shown in FIG. 7 of the drawings. Each entry in the pool of baby health profiles 700 is first classified into one of two groups where a first group 702 includes babies exhibiting neonatal encephalopathy and the second group 704 includes babies exhibiting an absence of neonatal encephalopathy 704. Following this, the entries in each group 702 704 are further divided into two groups wherein first groups 706 710 include babies exhibiting base deficit levels above a predetermined threshold and the second groups 708 718 including babies exhibiting base deficit levels below a predetermined threshold. It will readily be appreciated that the order of classification may be reversed without detracting from the spirit of the invention such that each entry in the pool of baby health profiles 700 is first classified on the basis of the base deficit level and then classified on the basis of the presence or absence of neonatal encephalopathy. The entries in group 706 are associated to class A, the entries in group 708 are associated to class B, the entries in group 710 are associated to class C and the entries in group 712 are associated to class D.

For each entry in the pool of baby health profiles 700, a record is generated including a first member indicative of a fetal heart rate signal and a second member indicative of the class assigned by the above described processed. Preferably, several entries in the pool of baby health profiles are associated to each of the classes such as to provide a suitable representation and observation set for the training of the artificial neural network. Generally, the fetal heart rate signals in the records have the same time duration. Extrapolation methods may be used to extend/shorter the length of a fetal heart rate signal where the signal does not have the desired time duration. The plurality of records generated in the above described manner forms the training set for the artificial neural network where the observations are derived from the fetal heart rate signal and the pre-defined outcomes are the assigned classes.

In the feature extraction step 602, for each record in the training set, the fetal heart rate signal is processed to derive a plurality of feature measures. In a non-limiting implementation, a feature extraction unit of the type described in connection with unit 300 (shown in FIG. 5 of the drawings) is used to generate a plurality of feature measures. The same feature measures used in the training of the neural network will be used when the neural network is used in the apparatus for monitoring the condition of a fetus 100.

In the conditioning of the neural network step 604, for each record in the training set, the plurality of feature measures are provided to respective inputs of the neural network. A simplified representation of the neural network is shown in FIG. 4. The input unit 400 of the network receives the feature measures. Each output in the set of outputs 404 406 408 410 is associated to a respective class. In non-limiting implementation, the neural network is a multilayer perceptron (MLP) network trained by backpropagation. For each record in the training set, the feature measures are presented to the input unit 400 of the network, the resulting outputs released by the set of outputs 404 406 408 410 are compared to the class in the record, and an error signal is generated. Using a standard backpropagation algorithm, this error is used to update the weights of the neural network such as to cause the output to reflect the class in the record. The training of a neural network in well known in the art an will not be described in further detail here.

SPECIFIC PHYSICAL IMPLEMENTATION

Those skilled in the art should appreciate that in some embodiments of the invention, all or part of the functionality previously described herein with respect to the apparatus for monitoring the condition of a fetus may be implemented as pre-programmed hardware or firmware elements (e.g., application specific integrated circuits (ASICs), electrically erasable programmable read-only memories (EEPROMs), etc.), or other related components.

In other embodiments of the invention, all or part of the functionality previously described herein with respect to the apparatus for monitoring the condition of a fetus may be implemented as software consisting of a series of instructions for execution by a computing unit. The series of instructions could be stored on a medium which is fixed, tangible and readable directly by the computing unit, (e.g., removable diskette, CD-ROM, ROM, PROM, EPROM or fixed disk), or the instructions could be stored remotely but transmittable to the computing unit via a modem or other interface device (e.g., a communications adapter) connected to a network over a transmission medium. The transmission medium may be either a tangible medium (e.g., optical or analog communications lines) or a medium implemented using wireless techniques (e.g., microwave, infrared or other transmission schemes).

Figure 10:
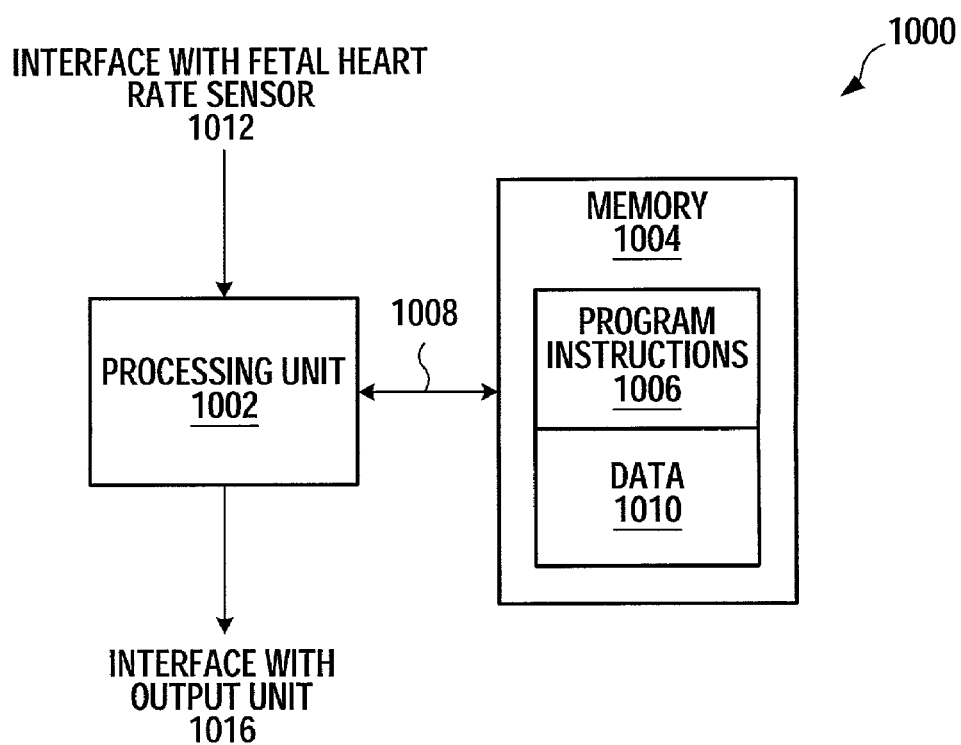
FIG. 10 is a block diagram of an apparatus for monitoring the condition of a fetus in accordance with a specific example of implementation of the present invention.

The computing unit implementing the apparatus for monitoring the condition of a fetus may be configured as a computing unit of the type depicted in FIG. 10, including a processing unit 1002 and a memory 1002 connected by a communication bus 1008. The memory includes data 1010 and program instructions 1006. The processing unit 1002 is adapted to process the data 1010 and the program instructions 1006 in order to implement the functional blocks described in the specification and depicted in the drawings. In a non-limiting implementation, the program instructions 1006 implement the functionality of processing unit 106 described above. The computing unit 1002 may also comprise a number of interfaces 1012 1016 for receiving or sending data elements to external devices. For example, interface 1012 may be used for receiving data streams indicative of a fetal heart rate signal and interface 1012 may be for releasing a signal causing a display unit to display of the results of the method implemented by program instructions 1006. An interface for receiving a signal indicative of uterine activity (not shown) may also be provided.

Those skilled in the art should further appreciate that the program instructions 1006 may be written in a number of programming languages for use with many computer architectures or operating systems. For example, some embodiments may be implemented in a procedural programming language (e.g., "C") or an object oriented programming language (e.g., "C++" or "JAVA").

It will be appreciated that the system for monitoring the condition of a fetus may be of a distributed nature where the fetal heart rate signal is collected at one location by a fetal heart rate sense and transmitted to a computing unit implementing the apparatus 100 over a network. The network may be any suitable network including but not limited to a global public network such as the Intranet, a private network and a wireless network. In addition, the computing unit implementing the apparatus 100 may be adapted to process multiple fetal heart rates originating from multiple fetuses concurrently using suitable methods known in the computer related arts.

Although the present invention has been described in considerable detail with reference to certain preferred embodiments thereof, variations and refinements are possible without departing from the spirit of the invention. Therefore, the scope of the invention should be limited only by the appended claims and their equivalents.

The invention claimed is:

1. An apparatus suitable for monitoring the condition of a fetus, said apparatus comprising:
   a) an input for receiving a signal indicative of a fetal heart rate;
   b) a processing unit coupled to said input, said processing unit being operative for processing said signal indicative of the fetal heart rate to derive data indicative of a degree of risk of developing a permanent neurological condition, the data indicative of the degree of risk of developing a permanent neurological condition indicating a likelihood that the condition of the fetus belongs to a class in a group of classes, the classes in the group of classes being associated with pre-defined fetal conditions characterized at least in part by:
      i. a measure of base deficit; and
      ii. a presence or absence of new-born encephalopathy;
   c) an output for releasing the data indicative of the degree of risk of developing a permanent neurological condition.

2. An apparatus as defined in claim 1, wherein said input is a first input, said apparatus comprising a second input for receiving a signal indicative of uterine activity, said processing unit being coupled to said first and second inputs and being operative for processing said signal indicative of the fetal heart rate and said signal indicative of uterine activity to derive the data indicative of a degree of risk of developing a permanent neurological condition.

3. An apparatus as defined in claim 1, wherein for each class in the group of classes, the data indicates a likelihood value that the condition of the fetus belongs to the corresponding class.

4. An apparatus as defined in claim 1, wherein said group of classes includes at least four classes comprising:
   a) a first class and a second class associated to respective pre-defined fetal conditions indicative of a presence of new-born encephalopathy; and
   b) a third class and a fourth class associated to respective pre-defined fetal conditions indicative of an absence of new-born encephalopathy.

5. An apparatus as defined in claim 4, wherein said first class is associated to a pre-determined fetal condition indicative of the presence of new-born encephalopathy and a measure of base deficit above a pre-determined level.

6. An apparatus as defined in claim 4, wherein said second class is associated to a pre-determined fetal condition indicative of the presence of new-born encephalopathy and a measure of base deficit below a pre-determined level.

7. An apparatus as defined in claim 4, wherein said third class is associated to a pre-determined fetal condition indicative of the absence of new-born encephalopathy and a base deficit measurement above a pre-determined level.

8. An apparatus as defined in claim 4, wherein said fourth class is associated to a pre-determined fetal condition indicative of the absence of new-born encephalopathy and a base deficit measurement below a pre-determined level.

9. An apparatus as defined in claim 1, wherein said group of classes includes at least four classes comprising:
   a) a first class associated to a pre-determined fetal condition indicative of the presence of new-born encephalopathy and a base deficit measurement above a pre-determined level;
   b) a second class associated to a pre-determined fetal condition indicative of the presence of new-born encephalopathy and a base deficit measurement below a pre-determined level;
   c) a third class associated to a pre-determined fetal condition indicative of the absence of new-born encephalopathy and a base deficit measurement above a pre-determined level;
   d) a fourth class associated to a pre-determined fetal condition indicative of the absence of new-born encephalopathy and a base deficit measurement below a pre-determined level.

10. An apparatus as defined in claim 1, wherein said processing unit includes a neural network.

11. An apparatus as defined in claim 10, wherein said neural network includes a plurality of inputs and a set of outputs, the outputs corresponding to respective classes in the group of classes, said neural network being adapted to release at each of said outputs a likelihood value associated to a respective class in the group of classes.

12. An apparatus as defined in claim 11, wherein said processing unit includes a pre-processing unit operative to:
    a) process the signal indicative of a fetal heart rate to derive a plurality of feature measures;
    b) providing said plurality of feature measures to the plurality of inputs of said neural network.

13. An apparatus as defined in claim 12, wherein said signal indicative of a fetal heart rate include heart rate information collected over a certain period of time.

14. An apparatus as defined in claim 13, wherein the certain period of time is in excess of 1 hour.

15. An apparatus as defined in claim 13, wherein the certain period of time is in excess of 2 hour.

16. An apparatus as defined in claim 13, wherein the certain period of time is in excess of 3 hour.

17. An apparatus as defined in claim 13, wherein the certain period of time is in excess of 4 hour.

18. A method suitable for monitoring the condition of a fetus, said method comprising:
    a) receiving a signal indicative of a fetal heart rate;
    b) processing said signal indicative of the fetal heart rate to derive data indicative of a degree of risk of developing a permanent neurological condition, the data indicative of the degree of risk of developing a permanent neurological condition indicating a likelihood that the condition of the fetus belongs to a class in a group of classes, the classes in the group of classes being associated with pre-defined fetal conditions characterized at least in part by:
   i. a measure of base deficit; and
   ii. a presence or absence of new-born encephalopathy;
c) releasing the data indicative of the degree of risk of developing a permanent neurological condition.

19. A method as defined in claim 18, said method further comprising:
   a) receiving a signal indicative of uterine activity;
   b) processing said signal indicative of the fetal heart rate and said signal indicative of uterine activity to derive the data indicative of a degree of risk of developing a permanent neurological condition.

20. A method as defined in claim 18, wherein for each class in the group of classes, the data indicates a likelihood value that the condition of the fetus belongs to the corresponding class.

21. A method as defined in claim 18, wherein said group of classes includes at least four classes comprising:
   a) a first class and a second class associated to respective pre-defined fetal conditions indicative of the presence of new-born encephalopathy; and
   b) a third class and a fourth class associated to respective pre-defined fetal conditions indicative of the absence of new-born encephalopathy.

22. A method as defined in claim 21, wherein said first class is associated to a pre-determined fetal condition indicative of the presence of new-born encephalopathy and a measure of base deficit above a pre-determined level.

23. A method as defined in claim 21, wherein said second class is associated to a pre-determined fetal condition indicative of the presence of new-born encephalopathy and a measure of base deficit below a pre-determined level.

24. A method as defined in claim 21, wherein said third class is associated to a pre-determined fetal condition indicative of the absence of new-born encephalopathy and a base deficit measurement above a pre-determined level.

25. A method as defined in claim 21, wherein said fourth class is associated to a pre-determined fetal condition indicative of the absence of new-born encephalopathy and a base deficit measurement below a pre-determined level.

26. A method as defined in claim 17, wherein said group of classes includes at least four classes comprising:
   a) a first class associated to a pre-determined fetal condition indicative of the presence of new-born encephalopathy and a base deficit measurement above a pre-determined level;
   b) a second class associated to a pre-determined fetal condition indicative of the presence of new-born encephalopathy and a base deficit measurement below a pre-determined level;
   c) a third class associated to a pre-determined fetal condition indicative of the absence of new-born encephalopathy and a base deficit measurement above a pre-determined level;
   d) a fourth class associated to a pre-determined fetal condition indicative of the absence of new-born encephalopathy and a base deficit measurement below a pre-determined level.

27. A method as defined in claim 17, wherein said method comprises processing said signal indicative of the fetal heart rate using a neural network to derive data indicative of a degree of risk of developing a permanent neurological condition.

28. A method as defined in claim 27, wherein said neural network includes a plurality of inputs and a set of outputs, the outputs corresponding to respective classes in the group of classes, said neural network being adapted to release at each of said outputs a likelihood value associated to a respective class in the group of classes.

29. A method as defined in claim 28, wherein said method comprises:
   a) processing the signal indicative of a fetal heart rate to derive a plurality of feature measures;
   b) providing said plurality of feature measures to the plurality of inputs of said neural network.

30. A method as defined in claim 29, wherein said signal indicative of a fetal heart rate include heart rate information collected over a certain period of time.

31. A method as defined in claim 30, wherein the certain period of time is in excess of 1 hour.

32. A method as defined in claim 30, wherein the certain period of time is in excess of 2 hour.

33. A method as defined in claim 30, wherein the certain period of time is in excess of 3 hour.

34. A method as defined in claim 30, wherein the certain period of time is in excess of 4 hour.

35. A computer readable storage medium including a program element suitable for execution by a computing apparatus for monitoring the condition of a fetus, said computing apparatus comprising:
   a) a memory unit;
   b) a processor operatively connected to said memory unit, said program element when executing on said processor being operative for:
      i. receiving a signal indicative of a fetal heart rate;
      ii. processing said signal indicative of the fetal heart rate to derive data indicative of a degree of risk of developing a permanent neurological condition, the data indicative of the degree of risk of developing a permanent neurological condition indicating a likelihood that the condition of the fetus belongs to a class in a group of classes, the classes in the group of classes being associated with pre-defined fetal conditions characterized at least in part by:
         (a) a measure of base deficit; and
         (b) a presence or absence of new-born encephalopathy;
      iii. releasing the data indicative of the degree of risk of developing a permanent neurological condition.

36. A computer readable storage medium as defined in claim 35, wherein said program element when executing on said processor being operative for:
   a) receiving a signal indicative of uterine activity;
   b) processing said signal indicative of the fetal heart rate and said signal indicative of uterine activity to derive the data indicative of a degree of risk of developing a permanent neurological condition.

37. A computer readable storage medium as defined in claim 35, wherein for each class in the group of classes, the data indicates a likelihood value that the condition of the fetus belongs to the corresponding class.

38. A computer readable storage medium as defined in claim 35, wherein said group of classes includes at least four classes comprising:
   a) a first class and a second class associated to respective pre-defined fetal conditions indicative of the presence of new-born encephalopathy; and
   b) a third class and a fourth class associated to respective pre-defined fetal conditions indicative of the absence of new-born encephalopathy.

39. A computer readable storage medium as defined in claim 38, wherein said first class is associated to a predetermined fetal condition indicative of the presence of new-born encephalopathy and a measure of base deficit above a pre-determined level.

40. A computer readable storage medium as defined in claim 38, wherein said second class is associated to a pre-determined fetal condition indicative of the presence of new-born encephalopathy and a measure of base deficit below a pre-determined level.

41. A computer readable storage medium as defined in claim 38, wherein said third class is associated to a pre-determined fetal condition indicative of the absence of new-born encephalopathy and a base deficit measurement above a pre-determined level.

42. A computer readable storage medium as defined in claim 38, wherein said fourth class is associated to a pre-determined fetal condition indicative of the absence of new-born encephalopathy and a base deficit measurement below a pre-determined level.

43. A computer readable storage medium as defined in claim 35, wherein said group of classes includes at least four classes comprising:
   a) a first class associated to a pre-determined fetal condition indicative of the presence of new-born encephalopathy and a base deficit measurement above a pre-determined level;
   b) a second class associated to a pre-determined fetal condition indicative of the presence of new-born encephalopathy and a base deficit measurement below a pre-determined level;
   c) a third class associated to a pre-determined fetal condition indicative of the absence of new-born encephalopathy and a base deficit measurement above a pre-determined level;
   d) a fourth class associated to a pre-determined fetal condition indicative of the absence of new-born encephalopathy and a base deficit measurement below a pre-determined level.

44. A computer readable storage medium as defined in claim 35, wherein said program element when executing on said processor being operative for implementing a neural network, the neural network being adapted to derive data indicative of a degree of risk of developing a permanent neurological condition.

45. A computer readable storage medium as defined in claim 44, wherein said neural network includes a plurality of inputs and a set of outputs, the outputs corresponding to respective classes in the group of classes, said neural network being adapted to release at each of said outputs a likelihood value associated to a respective class in the group of classes.

46. A computer readable storage medium as defined in claim 45, wherein said program element when executing on said processor being operative for:
   a) processing the signal indicative of a fetal heart rate to derive a plurality of feature measures;
   b) providing said plurality of feature measures to the plurality of inputs of said neural network.

47. A computer readable storage medium as defined in claim 46, wherein said signal indicative of a fetal heart rate include heart rate information collected over a certain period of time.

48. A computer readable storage medium as defined in claim 47, wherein the certain period of time is in excess of 1 hour.

49. A computer readable storage medium as defined in claim 47, wherein the certain period of time is in excess of 2 hour.

50. A computer readable storage medium as defined in claim 47, wherein the certain period of time is in excess of 3 hour.

51. A computer readable storage medium as defined in claim 47, wherein the certain period of time is in excess of 4 hour.

52. A trained neural network comprising:
   a) an input unit for receiving feature measures derived from a signal indicative of a fetal heart rate of a fetus; and
   b) a set of outputs associated to respective classes in a group of classes, the classes in the group of classes being associated with pre-defined fetal conditions characterized at least in part by:
      i. a measure of base deficit; and
      ii. a presence or absence of new-born encephalopathy;
   c) a processing core coupled to said input unit and to said set of outputs, said processing core being operative to process the feature measures received at said input unit, and to derive and release at each output data indicative of a likelihood that the condition of the fetus belongs to a respective class on the basis of the feature measures received at said input unit.

53. A trained neural network comprising as defined in claim 52, wherein said group of classes includes at least four classes comprising:
   a) a first class associated to a pre-determined fetal condition indicative of the presence of new-born encephalopathy and a base deficit measurement above a pre-determined level;
   b) a second class associated to a pre-determined fetal condition indicative of the presence of new-born encephalopathy and a base deficit measurement below a pre-determined level;
   c) a third class associated to a pre-determined fetal condition indicative of the absence of new-born encephalopathy and a base deficit measurement above a pre-determined level;
   d) a fourth class associated to a pre-determined fetal condition indicative of the absence of new-born encephalopathy and a base deficit measurement below a pre-determined level.

54. A computer readable storage medium including a program element suitable for execution by a computing apparatus for implementing a trained neural network, said trained neural network comprising:
   a) an input unit for receiving feature measures derived from a signal indicative of a fetal heart rate of a fetus;
   b) a set of outputs associated to respective classes in a group of classes, the classes in the group of classes being associated with pre-defined fetal conditions characterized at least in part by;
      i. a measure of base deficit; and
      ii. a presence or absence of new-born encephalopathy;
   c) a processing core coupled to said input unit and to said set of outputs, said processing core being operative to release at each output data indicative of a likelihood that the condition of the fetus belongs to a respective class on the basis of the feature measures received at said input unit.

55. A computer readable storage medium as defined in claim 54, wherein said group of classes includes at least four classes comprising:
   a) a first class associated to a pre-determined fetal condition indicative of the presence of new-born encephalopathy and a base deficit measurement above a pre-determined level;

b) a second class associated to a pre-determined fetal condition indicative of the presence of new-born encephalopathy and a base deficit measurement below a pre-determined level;
c) a third class associated to a pre-determined fetal condition indicative of the absence of new-born encephalopathy and a base deficit measurement above a pre-determined level;
d) a fourth class associated to a pre-determined fetal condition indicative of the absence of new-born encephalopathy and a base deficit measurement below a pre-determined level.

56. A fetal monitoring system comprising:
a) a sensor for receiving a signal indicative of a fetal heart rate;
b) an apparatus suitable for monitoring the condition of a fetus, said apparatus comprising:
  i an input coupled to said sensor for receiving a signal indicative of a fetal heart rate;
  ii. a processing unit coupled to said input, said processing unit implementing a neural network operative for processing said signal indicative of the fetal heart rate to derive data indicative of a degree of risk of developing a permanent neurological condition, the data indicative of the degree of risk of developing a permanent neurological condition indicating a likelihood that the condition of the fetus belongs to a class in a group of classes, the classes in the group of classes being associated with pre-defined fetal conditions characterized at least in part by:
    (a) a measure of base deficit; and
    (b) a presence or absence of new-born encephalopathy;
  iii. an output for releasing the data indicative of the degree of risk of developing a permanent neurological condition;
c) an output unit coupled to the output for said apparatus, said output unit being suitable for displaying the data indicative of the degree of risk of developing a permanent neurological condition.

57. An apparatus suitable for monitoring the condition of a fetus, said apparatus comprising:
a) means for receiving a signal indicative of a fetal heart rate;
b) means for processing said signal indicative of the fetal heart rate to derive data indicative of a degree of risk of developing a permanent neurological condition, the data indicative of the degree of risk of developing a permanent neurological condition indicating a likelihood that the condition of the fetus belongs to a class in a group of classes, the classes in the group of classes being associated with pre-defined fetal conditions characterized at least in part by:
  i. a measure of base deficit; and
  ii. a presence or absence of new-born encephalopathy;
c) means for releasing the data indicative of the degree of risk of developing a permanent neurological condition.

58. An method for training a neural network suitable for monitoring the condition of a fetus, said method comprising:
a) receiving a plurality of records, each record comprising:
  i. a first entry indicative of a fetal heart rate signal;
  ii. a second entry indicative of a class selected from a group of classes, the classes in said group of classes being associated with pre-defined fetal conditions characterized at least in part by:
    (a) a measure of base deficit; and
    (b) a presence or absence of new-born encephalopathy;
b) conditioning the neural network on the basis of the first and second entries of each record such as to enable the neural network, upon reception of a signal indicative of a fetal heart rate to derive a likelihood that the condition of the fetus belongs to a class in the group of classes.

59. A method as defined in claim 58, wherein said group of classes includes at least four classes comprising;
a) a first class associated to a pre-determined fetal condition indicative of the presence of new-born encephalopathy and a base deficit measurement above a pre-determined level;
b) a second class associated to a pre-determined fetal condition indicative of the presence of new-born encephalopathy and a base deficit measurement below a pre-determined level;
c) a third class associated to a pre-determined fetal condition indicative of the absence of new-born encephalopathy and a base deficit measurement above a pre-determined level;
d) a fourth class associated to a pre-determined fetal condition indicative of the absence of new-born encephalopathy and a base deficit measurement below a pre-determined level.

60. A method as defined in claim 59, wherein said method comprises conditioning the neural network on the basis of said first and second entries of each record such as to enable the neural network, upon reception of a signal indicative of a fetal heart rate to assign likelihood values to each class in the group of classes, at least in part on the basis of the signal indicative of a fetal heart rate.

61. A method as defined in claim 60, wherein said neural network includes a plurality of inputs and a set of outputs, the outputs corresponding to respective classes in the group of classes, said method comprising:
a) processing the signal indicative of a fetal heart rate to derive a plurality of feature measures;
b) providing said plurality of feature measures to the plurality of inputs of said neural network.

62. A neural network conditioned on the basis of the method described in claim 58.

63. An apparatus suitable for monitoring the condition of a fetus, said apparatus comprising:
a) an input for receiving a signal indicative of a fetal heart rate;
b) a feature extraction unit coupled to said input, said feature extraction unit being operative for processing the signal indicative of the fetal heart rate to derive feature measures;
c) a neural network module coupled to said feature extraction unit, said neural network being operative to process the feature measures to derive data indicative of a degree of risk of developing a permanent neurological condition, the data indicative of the degree of risk of developing a permanent neurological condition indicating a likelihood that the condition of the fetus belongs to a class in a group of classes, the classes in the group of classes being associated with pre-defined fetal conditions characterized at least in part by:
  i. a measure of base deficit; and
  ii. a presence or absence of new-born encephalopathy;
d) an output for releasing the data indicative of the degree of risk of developing a permanent neurological condition.

64. An apparatus as defined in claim 63, wherein said feature extraction unit is operative for:

a) processing said fetal heart rate to identifying a plurality of feature events;
b) generating a plurality of feature measures for the plurality of feature events identified in a);
c) summarising said plurality of feature measures to generate a compact representation of feature measures;
d) providing the compact representation of feature measures to said neural network module.

65. An apparatus as defined in claim 64, wherein summarising said plurality of feature measures to generate a compact representation of feature measures includes:
a) processing the plurality of feature measures to generate at least one interpolated feature measure signal;
b) decimating the interpolated feature measure signal such as to generate the compact representation of feature measures.

66. An apparatus as defined in claim 65, wherein decimating the interpolated feature measure signal is effected on the basis of regular sampling intervals.

67. An apparatus as defined in claim 65, wherein decimating the interpolated feature measure signal is effected on the basis of irregular sampling intervals.

68. An apparatus as defined in claim 64, wherein the plurality of feature events includes at least some events selected from the set consisting of baseline, acceleration, deceleration and contraction events.

69. An apparatus as defined in claim 68, wherein subsets of the plurality of feature measures are associated to respective feature events, at least one subset being associated to a baseline feature event, said at least one subset including feature measures selected from the set consisting of mean value, frequency, length, variability and sinusoidal pattern.

70. An apparatus as defined in claim 68, wherein subsets of the plurality of feature measures are associated to respective feature event, at least one subset being associated to an acceleration feature event, said at least one subset including feature measures selected from the set consisting of mean value, frequency, length, variability and area.

71. An apparatus as defined in claim 68, wherein subsets of to plurality of feature measures are associated to respective feature events, at least one subset being associated to a contraction feature event, said at least one subset including a feature measure selected from the set consisting of frequency and deceleration recovery time.

72. An apparatus as defined in claim 64, wherein said group of classes includes at least four classes comprising:
a) a first class associated to a pre-determined fetal condition indicative of the presence of new-born encephalopathy and a base deficit measurement above a pre-determined level;
b) a second class associated to a pre-determined fetal condition indicative of the presence of new-born encephalopathy and a base deficit measurement below a pre-determined level;
c) a third class associated to a pre-determined fetal condition indicative of the absence of new-born encephalopathy and a base deficit measurement above a pre-determined level;
d) a fourth class associated to a pre-determined fetal condition indicative of the absence of new-born encephalopathy and a base deficit measurement below a pre-determined level.

73. An apparatus as defined in claim 63, wherein said neural network module includes a plurality of inputs and a set of outputs, the outputs corresponding to respective classes in the group of classes, said neural network module being adapted to release at each of said outputs a likelihood value associated to a respective class in the group of classes.

74. An apparatus as defined in claim 73, wherein the compact representation of feature measures is provided to the plurality of inputs of said neural network module.

75. An apparatus suitable for monitoring the condition of a fetus, said apparatus comprising:
a) an input for receiving a signal indicative of a fetal heart rate;
b) a processing unit coupled to said input, said processing unit being operative for processing said signal indicative of the fetal heart rate to derive data indicative of a degree of risk of developing a permanent neurological condition, the data indicative of the degree of risk of developing a permanent neurological condition indicating a likelihood that the condition of the fetus belongs to a class in a group of classes, the classes in the group of classes being associated with pre-defined fetal conditions characterized at least in part by a measure of base deficit and a presence or absence of a new-born encephalopathy, the group of classes comprising
  i. a first class associated with a high risk of developing a permanent neurological condition;
  ii. a second class associated with a low risk of developing a permanent neurological condition;
  iii. at least another class associated with an intermediate risk of developing a permanent neurological condition;
c) an output for releasing the data indicative of the degree of risk of developing a permanent neurological condition.

* * * * *